United States Patent
Spicer

(10) Patent No.: US 8,173,613 B2
(45) Date of Patent: May 8, 2012

(54) MODULATION OF MESENCHYMAL AND METASTATIC CELL GROWTH

(75) Inventor: Douglas B. Spicer, Cape Elizabeth, ME (US)

(73) Assignee: Maine Medical Center, Scarborough, ME (US)

( * ) Notice: Subject to any disclaimer, the term of this patent is extended or adjusted under 35 U.S.C. 154(b) by 0 days.

(21) Appl. No.: 11/525,715

(22) Filed: Sep. 22, 2006

(65) Prior Publication Data

US 2007/0093442 A1      Apr. 26, 2007

Related U.S. Application Data

(60) Provisional application No. 60/719,386, filed on Sep. 22, 2005.

(51) Int. Cl.
| | |
|---|---|
| C12N 15/11 | (2006.01) |
| C12N 15/00 | (2006.01) |
| C12N 5/02 | (2006.01) |
| A61K 48/00 | (2006.01) |
| A61K 39/00 | (2006.01) |
| C07H 21/04 | (2006.01) |

(52) U.S. Cl. .................... 514/44 A; 435/320.1; 435/325; 424/93.1; 424/277.1; 536/24.5

(58) Field of Classification Search .......... None
See application file for complete search history.

(56) References Cited

U.S. PATENT DOCUMENTS

| | | | |
|---|---|---|---|
| 5,107,065 A | 4/1992 | Shewmaker et al. | |
| 5,457,189 A | 10/1995 | Crooke et al. | |
| 5,605,793 A | 2/1997 | Stemmer et al. | |
| 6,060,596 A | 5/2000 | Lerner | |
| 6,185,506 B1 | 2/2001 | Cramer et al. | |
| 6,303,374 B1 | 10/2001 | Zhang et al. | |
| 6,377,895 B1 | 4/2002 | Horlbeck | |
| 6,537,776 B1 | 3/2003 | Short | |
| 6,566,501 B1 | 5/2003 | Amar | |
| 6,610,663 B2 | 8/2003 | Cook et al. | |
| 6,737,512 B2 | 5/2004 | Wu et al. | |
| 6,936,477 B2 | 8/2005 | Still et al. | |

OTHER PUBLICATIONS

Castanon et al., 2001, Development 128:3145-3159.*
Goncalves et al, 2005, Bioessays, 27: 506-517.*
Yang et al., 2004, Cell 117:927-939.*
Verzi et al., 2002, Dev. Biology 249:174-190.*
Martinez et al., 2002, Cell 110:563-574.*
Shipps, et al., Proc. Natl. Acad. Sci. USA, 94:11833-11838, 1997.
Stockwell, et al., Chemistry & Biology, 6:71-83, 1999.
Bao, S., et al., Cancer Cell, 5:329-339, 2004.
Iruela-Arispe, M.L., et al., Int J Biochem Cell Biol, 36:1070-1078, 2004.
Hayashido, et al., Int J Mol Med., 12:447-452, 2003.

(Continued)

*Primary Examiner* — Robert M Kelly
*Assistant Examiner* — Kelaginamane Hiriyanna
(74) *Attorney, Agent, or Firm* — Pierce Atwood LLP; Kevin M. Farrell, Esq.; David J. Wilson, Esq.

(57) ABSTRACT

The present invention relates to compositions and methods for the modulation of metastatic and mesenchymal cell growth and mobility via the regulation of the formation of Twist/Twist homodimers and Twist/E heterodimers. The present invention also relates to methods for screening agents and compound libraries for molecules that function to modulate the formation of Twist/Twist homodimers, Twist/E protein heterodimers or their upstream or downstream effector molecules.

5 Claims, 13 Drawing Sheets

OTHER PUBLICATIONS

Fields S, Song O.K. A novel genetic system to detect protein-protein interactions. Nature 340:245-6;1989.
Ghouzzi, et al., Nat Genet 15:42-6, 1997.
Gripp, et al., Hum Mutat 15:479, 2000.
Bourgeois et al., Hum Mol Genet 7:945-957, 1998.
Carver, et al., Anat Rec 268:90-92, 2002.
Stankiewicz, et al., Am J Med Genet 103:56-62, 2001.
Castanon and Baylies, Gene 287, 11-22, 2002.
O'Rourke and Tam, Int J Dev Biol 46, 401-13, 2002.
Massari and Murre, Mol Cell Biol 20:429-440, 2000.
Vinals, et al., Embo J 23:3527-3537, 2004.
Vinals and Ventura, J Biol Chem 279:45766-45772, 2004.
Castanon, et al., Development 128:3145-3159, 2001.
Johnson, et al., Mech Dev 91:341-345, 2000.
Rice, et al., Development 127:1845-1855, 2000.
Funato, et al., Mol Cell Biol 21:7416-7428, 2001.
Lin, et al., Am. J. Pathol, 163:2113-2126, 2003.
Maestro, et al., Genes Dev. 13:2007-2217, 1999.
Sigvardsson, M., et al., Immunity 7:25-36, 1997.
Bakiri, L., et al., Mol Cell Biol, 22:4952-4964, 2002.
Spicer et al., Science 27:1476-1480, 1996.
Serrano et al., Cell 88:593-602, 1997.
Hardy et al., J Virol 71:1842-1849, 1997.
Lassar et al., Cell 66:305-315, 1991.
Novitch et al., Curr Biol 9:449-59, 1999.
Leshem et al., J Cell Physiol 184:101-9, 2000.
Araki et al., Proc Natl Acad Sci, U S A 92:160-4, 1995.
Lyden et al., Nature 401:670-677, 1999.
Isaac et al., Mech Dev 93:41-8, 2000.
Yoshida et al., J Anat 206:437-44, 2005.
Chun et al., Am J Med Genet 110:136-43, 2002.
Paznekas et al., Am J Hum Genet 62:1370-80, 1998.
Oshima et al., J Cell Biochem 86:792-804, 2002.
Benezra et al., Cell 61:49-59, 1990.
Neuhold and Wold, Cell 74:1033-42, 1993.
Sigvardsson et al., Immunity 7:25-36, 1997.
Ogata et al., Proc Natl Acad Sc,i U S A 90:9219-22, 1993.
Volpert et al., Cancer Cell 2:473-83, 2002.
Jiang et al., Dev Biol 241:106-16, 2002.
Lee et al., J Cell Biochem 75:566-77, 1999.
Yousfi et al., J Clin Invest 107:1153-1161, 2001.
Bialek et al., Dev Cell 6:423-35, 2004.
Oram and Gridley, Genetics 170:971-974, 2005.
Yang, et al., Cell, 2004, 117:927-939, 2004.
Jessen, et al., Cancer Res. 6:R157-169, 2004.
Howard, et al., Nat Genet 15:36-41, 1997.
Elias, M.C., Tozer KR, Silver JR, Mikheeva S, Deng M, Morrison RS, Manning TC, Silbergeld DL, Glackin CA, Reh TA, Rostomily RC. TWIST is expressed in himan gliomas and promotes invasion. Neoplasia. Sep. 2005;7(9):824-37. (entire article).
Kwok, W.K., Ling MT, Lee TW, Lau TC, Zhou C, Zhang X, Chua CW, Chan KW, Chan FL, Glackin C, Wong YC, Wang X. Up-regulation of TWIST in prostate cancer and its implication as a therapeutic target. Cancer Res. Jun. 15, 2005:65(12):5153-62. (entire article).
Karreth, F., Tuveson DA. Twist induces an epithelial-mesenchymal transition to facilitate tumor metastatis. Cancer Biol Ther. Nov. 2004;3(11):1058-9. Epub Nov. 12, 2004. (entire article).
Connerney, J., Andreeeva V, Leshem Y, Muentener C, Mercado MA, Spicer DB. Twist May;235(5):1345:57. (entire article), year 2006.

* cited by examiner a) Periostin sagittal WT b) Periostin coronal WT c) Periostin sagittal Twist +/- d) Periostin coronal Twist +/- e) TSP1 sagittal WT f) TSP1 coronal WT g) TSP1 sagittal Twist +/- h) TSP1 coronal Twist +/- i) FGFR2 sagittal WT j) FGFR2 coronal WT k) FGFR2 sagittal Twist +/- l) FGFR2 coronal Twist +/- m) Periostin    TSP-1 frontal
coronal
sagittal n) Id sagittal         Twist sagittal

| Genotype | n | CI ± S.E.M. | Penetrance (%) |
|---|---|---|---|
| Wild Type | 21 | 0.02 ± 0.02 | 0.05 |
| Tw+/- | 17 | 1.64 ± 1.27 | 87.50 |
| Tw+/- ; Id1+/- | 29 | 0.85 ± 1.46 | 75.86 |
| Tw+/- ; Id1-/- or Tw+/- ; Id1+/- ; Id3+/- | 21 | 0.07 ± 0.07 | 4.75 |
| Tw+/- ; Id1-/- ; Id3+/- | 5 | 0 | 0 |

Craniosynostosis in progeny of the Twist1 +/- X Id1-/- ; Id3+/- cross at 5 weeks. Skulls were assessed using a scoring system in which a suture was assigned a value from 0 to 3: 0 = completely unfused; 1 = <50% fused; 2 = >50% fused; 3 = 100% fused. Left and right coronal sutures were scored individually for each skull. For each genotype the scoring mean ±S.E.M. was determined, and was termed the craniosynostosis index (CI). Statistical analysis was performed by one way ANOVA. The difference between Tw+/- and Tw+/- mice which lost two copies of Id was highly significant ($P<10^{-15}$). Penetrance was calculated as the percentage of animals that exhibited any coronal suture fusion.

Figure 14

SEQUENCE LISTING

```
<160> NUMBER OF SEQ ID NOS: 15

<210> SEQ ID NO 1
<211> LENGTH: 87
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 1
ggtaccggcg gaggctcgag cggtgggagc ggcggagggt ccggcggagg ctcgagcggt     60
gggagcggcg gagggtccgg cgaattc                                         87

<210> SEQ ID NO 2
<211> LENGTH: 28
<212> TYPE: DNA
<213> ORGANISM: Mus musculus

<400> SEQUENCE: 2
ggtggatcca ccatgaaggt cgccagtg                                        28

<210> SEQ ID NO 3
<211> LENGTH: 28
<212> TYPE: DNA
<213> ORGANISM: Mus musculus

<400> SEQUENCE: 3
tggatccgtc catctggtcc ctcagtgc                                        28

<210> SEQ ID NO 4
<211> LENGTH: 18
<212> TYPE: DNA
<213> ORGANISM: Mus musculus

<400> SEQUENCE: 4
aggcgctgag cccggtgc                                                   18

<210> SEQ ID NO 5
<211> LENGTH: 17
<212> TYPE: DNA
<213> ORGANISM: Mus musculus

<400> SEQUENCE: 5
cgggaggtgc caggacg                                                    17

<210> SEQ ID NO 6
<211> LENGTH: 24
<212> TYPE: DNA
<213> ORGANISM: Mus musculus

<400> SEQUENCE: 6
ctgtgccgaa tgaagaacac gacc                                            24

<210> SEQ ID NO 7
<211> LENGTH: 22
```

```
<212> TYPE: DNA
<213> ORGANISM: Mus musculus

<400> SEQUENCE: 7
caaagtctgc tatcttcatc ac                                              22

<210> SEQ ID NO 8
<211> LENGTH: 24
<212> TYPE: DNA
<213> ORGANISM: Mus musculus

<400> SEQUENCE: 8
aaggacaaac ccaaccgtgt gacc                                            24

<210> SEQ ID NO 9
<211> LENGTH: 22
<212> TYPE: DNA
<213> ORGANISM: Mus musculus

<400> SEQUENCE: 9
caaagtctgc tatcttcatc ac                                              22

<210> SEQ ID NO 10
<211> LENGTH: 20
<212> TYPE: DNA
<213> ORGANISM: Mus musculus

<400> SEQUENCE: 10
cggccagcac tatctacaca                                                 20

<210> SEQ ID NO 11
<211> LENGTH: 20
<212> TYPE: DNA
<213> ORGANISM: Mus musculus

<400> SEQUENCE: 11
gtctgtgacc acagccacat                                                 20

<210> SEQ ID NO 12
<211> LENGTH: 20
<212> TYPE: DNA
<213> ORGANISM: Mus musculus

<400> SEQUENCE: 12
tgcgacttca acagcaactc                                                 20

<210> SEQ ID NO 13
<211> LENGTH: 20
<212> TYPE: DNA
<213> ORGANISM: Mus musculus

<400> SEQUENCE: 13
gatggaaatt gtgagggaga                                                 20

<210> SEQ ID NO 14
<211> LENGTH: 6
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 14 cagcat                                                                 6
```

```
<210> SEQ ID NO 15
<211> LENGTH: 29
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 15

Gly Thr Gly Gly Gly Ser Ser Gly Gly Ser Gly Gly Gly Ser Gly Gly
 1               5                  10                  15

Gly Ser Ser Gly Gly Ser Gly Gly Gly Ser Gly Glu Phe
            20                  25
```

MODULATION OF MESENCHYMAL AND METASTATIC CELL GROWTH

The present invention was supported in whole or in part by NIH grant numbers P20 RR15555 and R01 DE015329. The government may have certain rights in the invention.

BACKGROUND

Modulation of cell growth is critical to the development and health of organisms. Aberrant growth of cells, i.e., the increase or decrease of cell growth rates, may lead to numerous disease states including metastatic cancers (leading examples of which are breast cancer, prostate cancer, lung cancer and metastatic melanoma) and developmental defects characterized by either increased or decreased mesenchymal cell growth (e.g., craniosynostosis, cleft lip, cleft palate, wound healing, wasting diseases and muscular dystrophies).

Breast cancer and prostate cancers are among the most common human cancers in the United States affecting up to 1 in 8 women and 1 in 6 men, respectively. Tumor metastasis is the major cause of death from these cancers and, while there have been improvements in diagnosis and treatment, it is still unclear what the molecular changes are that are likely to lead to metastasis and tissue invasion. The understanding of such mechanisms would aid in finding compositions and methods for the partial or complete inhibition of metastasis and tumor invasion.

Craniosynostosis is a fairly common disorder occurring in about 1 in 2500 individuals wherein there is a premature fusion of the sutures of the cranium. Children that have this condition often suffer from restricted skull growth resulting in increased pressure on the brain, vision problems and behavioral problems. Surgical intervention is risky and expensive requiring a team of highly trained specialists. As with uncontrolled metastatic growth, the understanding of the underlying causes of under or unregulated non-metastatic cell growth will be instrumental in finding compositions and techniques for the treatment of resulting medical conditions.

As both metastatic cancers and developmental disease states involve the misregulation of cell growth it is possible that both types of conditions may be the result of similar underlying molecular causes. If this is the case then similar therapeutic approaches may be effective for both metastatic cancers and developmental disease states. Therefore, what is needed is the identification of the underlying causes of metastasis and developmental misregulation as well as the development of methods for the modulation of metastatic and mesenchymal cell growth and the screening of agents effective in the modulation of metastatic and mesenchymal cell growth.

SUMMARY OF THE INVENTION

The present invention relates to compositions and methods for the modulation of metastatic and mesenchymal cell growth and mobility via the regulation of the formation of Twist/Twist homodimers and Twist/E heterodimers or their upstream or down stream effector molecules. The present invention also relates to methods for screening agents and compound libraries for molecules that function to modulate the formation of Twist/Twist homodimers, Twist/E protein heterodimers or their upstream or downstream effector molecules.

The present invention is related to the novel discovery that Twist (a basic-Helix-Loop-Helix (bHLH) transcription factor) plays both positive and negative roles in the regulation of early morphogenesis and differentiation of mesenchymal tissues by forming functional Twist/Twist homodimers. Small changes in Twist expression have profound phenotypic effects as exemplified by TWIST haploinsufficiency resulting in craniofacial and limb abnormalities. The present invention also demonstrates that the modulation of Twist/Twist homodimer formation is instrumental in the regulation of tumor cell growth and the control of tumor metastasis. Thus, the present invention provides compositions and methods for the modulation and control of cell growth and mobility via the regulation of functional Twist/Twist (T/T) homodimers and Twist/E protein (T/E) heterodimers.

The present invention relates to the novel discovery by the inventor that Twist is nearly unique in that it is a transcription factor found to form functional homodimers and that it is instrumental it that it regulates cell growth via the modulation of numerous downstream molecules. Although the present invention is not limited to any particular theory or mechanism, it is believed that the ability of Twist to form Twist/Twist homodimers is regulated via a competitive mechanism wherein the amount of free Twist is controlled by the sequestering of Twist by E protein. Furthermore, the amount of E protein available to bind Twist is controlled by the binding of E protein by Id, a non-basic HLH protein (HLH). In other words, Twist and Id compete for E protein binding. The more free E protein available (and/or the less Id protein available), the more likely it is that Twist will form T/E heterodimers and the less likely it is that Twist will form T/T homodimers. In one aspect of the invention, the control of cell growth and mobility (or, in the case of cancerous cells, uncontrolled growth and metastasis) is regulated by the ratio of T/T homodimers to T/E heterodimers, wherein the higher the ratio of T/T to T/E dimers leads to cell growth and/or cell mobility. In another aspect of the present invention, metastatic cells and mesenchymal cells are regulated by the downstream effector molecules of T/T and T/E dimers.

In another embodiment of the present invention, it is contemplated that Twist expression and E protein expression are controlled with small inhibitory RNA (siRNA) molecules. Such molecules bind to translated mRNA and block transcription and, thus, can be used, for example, as therapeutic agents. Also, the inhibition of Twist and E protein expression and function can be modulated by agents that inhibit or enhance the function of upstream or downstream effector molecules. (As used herein, an "effector molecule" is a molecule, chemical, or structure that regulates a pathway by increasing or decreasing the pathway's reaction rate). Such molecules can be identified by methods of the present invention wherein, for example, combinatorial chemical libraries are screened for molecules with abilities to bind Twist, E protein or Id and thereby inhibit or enhance their binding function and, thus, their downstream effect. Also, such molecules may exert their ability to modulate T/T homodimer formation by interacting with upstream or downstream effector molecules of Twist, E protein or Id function.

DESCRIPTION OF FIGURES

FIG. 14 shows craniosynostosis in progeny of the Twist1 +/− x Id1 −/−; Id3 +/− cross at 5 weeks.

DETAILED DESCRIPTION OF THE INVENTION

Figure 1A:
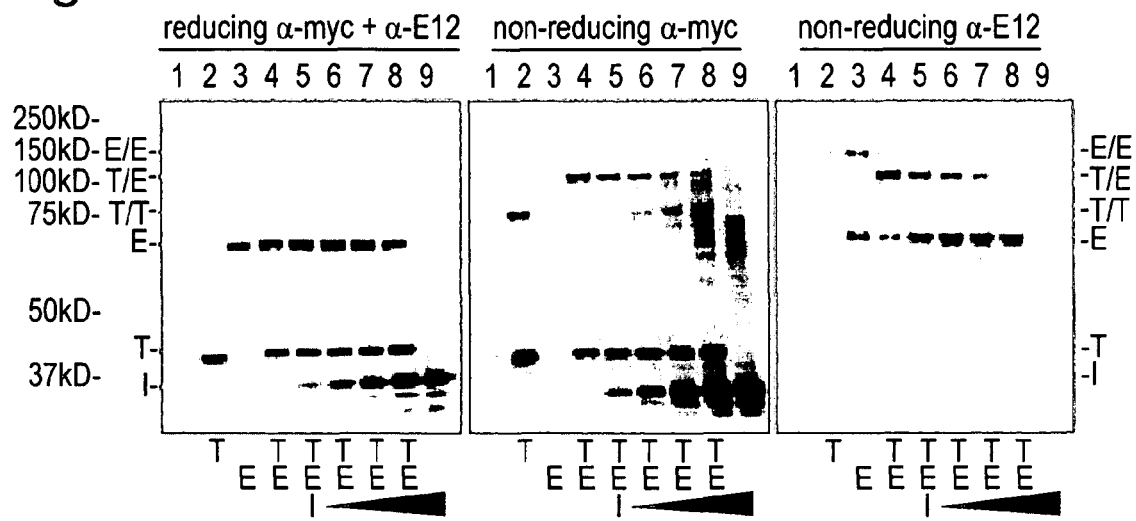
FIG. 1 shows Id levels alter the ratio of T/T and T/E dimers. (a) 293 cells were transfected with Twist (T), E12 (E), and Id1 (I)-expressing plasmids as indicated. Id1 levels were 0.25, 0.5, 1 and 2-fold the level of Twist and E12 in lanes 5-8, respectively. For the two right gels samples were prepared without β-mercaptoethanol and were not heated prior to loading but were the same as the reducing gel on the left in all other respects. The Twist and the Id1 proteins contained myc-epitope tags and were detected with 9E10 anti-myc monoclonal antibodies in the left and right blots. E12 proteins were detected with anti-E2a polyclonal antibody in the center and right blots. The sizes for the T, E, and I monomers and the T/T, T/E and E/E dimers are indicated on the sides. (b) Diagram depicting the structure of the "forced dimers." Two Twist monomers or Twist and E12 monomers are linked in frame by a 29 amino acid linker. (c) In vitro translated proteins were utilized in an electrophoretic mobility shift assay (EMSA) using the bHLH binding site (E Box) from the MCK gene as a probe. 0.5, 1 and 2 fold amounts of Id1 protein were added to reactions with either the TE heterodimer (TE) or with separate Twist (T) and E12 (E) proteins where indicated. Lysate control (L). (d) EMSA analysis as in (c) where 0.5, 1 and 2 fold amounts of E12 protein were added to reactions with either the homodimer (TT) or with the Twist (T) protein where indicated.

The present invention relates to methods for the modulation (i.e., the partial or total inhibition or promotion) of cell growth. In one aspect, the present invention relates to the modulation of metastatic cancer growth. Non-limiting examples are breast cancer, prostate cancer, lung cancer and metastatic melanoma. Such modulation of metastatic cell growth may be for investigational or therapeutic purposes. In another aspect, the present invention relates to the modulation of cell growth of cells of mesenchymal origin. Examples are the promotion or inhibition of, for example, bone growth such as for the investigation and treatment of diseases such as, but not limited to, craniosynostosis, cleft lip, cleft palate, wound healing, wasting diseases and muscular dystrophies. The mesenchymal or metastatic cells preferably are found in an organism. The organism is preferably a mammal and more preferably a human. Said cells of mesenchymal origin may be, but need not be, metastatic. Metastatic cells need not be of mesenchymal origin. The cell growth of the present invention (either metastatic or mesenchymal cell growth) is modulated, promoted or inhibited via the regulation of the formation of homodimers made of Twist proteins (T/T dimers) as well as the formation of heterodimers made of Twist protein and E protein (T/E dimers). Therefore, the present invention contemplates that Twist/Twist and Twist/E protein dimer formation and modulation is a target for therapeutic intervention. In one aspect, the present invention modulates the ratio of Twist/Twist homodimers to Twist/E heterodimers, wherein the up regulation of Twist/Twist homodimer formation and/or the down regulation of Twist/E heterodimer formation is associated with an increase in metastatic or mesenchymal cell growth (e.g., the promotion of bone growth or of metastatic cancers) and the up regulation of Twist/E heterodimer formation and/or the down regulation of Twist/Twist homodimer formation is associated with the decrease of metastatic or mesenchymal cell growth (e.g., the inhibition of bone growth or of metastatic cancers). The present invention also relates to modulation of cell growth by contacting the cells in which the modulation of cell growth is desired with small molecule agents or compositions known or suspected of modulating the interaction of Twist with E proteins or other Twist proteins: that is, suspected of regulating the formation of Twist/Twist homodimers and/or Twist/E heterodimers or suspected of regulating the function of T/T and/or T/E dimers. The present invention is not limited by the mechanism by which said small molecule agents or compositions modulate the formation of Twist/Twist homodimers or Twist/E heterodimers. Such mechanisms may include, but are not limited to, interacting directly with Twist proteins or E proteins, interacting with up stream regulators of the Twist or E proteins or interacting with down stream effector molecules activated via (directly or indirectly) the formation of said Twist/Twist homodimers and/or Twist/E heterodimers.

Additionally, the present invention relates to the screening of small molecule (e.g., combinatorial chemical) libraries for the detection of agents effective in the regulation of T/T and/or T/E dimer formation and/or the modulation of downstream and upstream effectors of T/T and/or T/E function as compared to, for example, T/T and/or T/E formation in experiment or historic controls. Other examples of agents effective in the modulation of T/T and/or T/E formation and function are small inhibitory RNA (siRNA) molecules and Twist and/or E proteins modified by, for example, protein engineering or directed molecular evolution. As detailed below, all of these procedures are well know to those skilled in the art.

Twist Involvement in Metastatic Cell Growth

In one aspect, the present invention contemplates a method for inhibiting metastatic cell growth in an organism, the method comprising contacting the cells with an agent characterized by the ability to decrease the ratio of Twist/Twist homodimers to Twist/E heterodimers in the organism. The decrease of the ratio of Twist/Twist homodimers to Twist/E heterodimers can be used in therapies for the treatment of metastatic cancer including, e.g., breast, prostate and lung cancers and metastatic melanoma, etc. The organism that has metastatic cell growth is, in a preferred embodiment, a mammal. In a more preferred embodiment, the organism is a human. The agent used to contact the metastatic cells can be any agent that is effective in decreasing the ratio of Twist/Twist homodimers to Twist/E heterodimers. Such agents can be administered to the organism by techniques known in the art including, but not limited to, injection (e.g., subcutaneous, intramuscular, vascular, etc.) wherein they type of injection is determined by the type of metastatic growth to be treated. Such agents can also be administered by infusion into, for example, the blood stream or the target organ or other target location. In other embodiments, the agents are administered orally. The agent may comprise other reagents to aid in the administration, manufacture, storage and transport of the agent including, but not limited to, binders, stabilizers, colors, flavors, buffers, excipients, etc. The organism that is the recipient of the agent can then be monitored for the decrease in the ratio of Twist/Twist to Twist/E dimers. Samples for monitoring may be acquired by blood draws, biopsies, etc. The detection of the decrease in the ratio of Twist/Twist to Twist/E dimers can be detected by, for example, SDS-PAGE gel electrophoresis, Western blotting, or other immunohistochemical techniques (e.g., ELISA, RIA or FACS assays) or other suitable assays known in the art.

In one embodiment, the agent is a small molecule characterized by the ability to decrease the ratio of Twist/Twist homodimers to Twist/E heterodimers by promoting Twist/E heterodimerization or by inhibiting Twist/Twist homodimerization. The agent(s) to be administered to the organism can be selected from, for example, small molecule libraries (e.g., combinatorial chemical libraries). Such libraries are known in the art and are commercially available.

Techniques are known to those skilled in the art for the selection of agents from such libraries. In the present embodiment, the agent is being screened for its ability to decrease the ratio of Twist/Twist homodimers to Twist/E heterodimers either by promoting Twist/E heterodimerization or by inhibiting Twist/Twist homodimerization. The present invention is not limited by the nature of the screening method. For example, in certain embodiments, the present invention contemplates screening methods wherein Twist and/or E protein is bound to a solid surface, test agents are contacted to the Twist and/or E protein and agents that bind to the Twist and/or E proteins are detected. Such detection may utilize, for example, immunological methods, radiolabeling of the test agents, fluorescent or other tags (e.g., streptavidin or myc-tagged labeled molecules), etc. Examples of using tagged molecules to monitor Twist and E dimer formation are given in the Examples section. Additionally, the yeast two-hybrid system (Fields S, Song O. K. A novel genetic system to detect protein-protein interactions. *Nature* 340:245-6, 1989; incorporated herein by reference) can be used to agents that decrease the ratio of Twist/Twist homodimers to Twist and E heterodimers. In other embodiments, the assay is performed in solution. In other assays, for example, the agent suspected of decreasing the ratio of Twist/Twist homodimers to Twist/E heterodimers is added to a mixture of Twist and E protein and dimer formation is compared to a control mixture without the test agent added. Additionally, the identification and effectiveness of the agents may be determined by comparing, for example, by the downstream effect of the agent (e.g., the effect on cell growth and/or mobility) as compared to, for example, similar cells not exposed to the test agent or similar cells comprising another suitable control. Effective agents may work, for example, by binding to Twist or E protein as competitive or non-competitive inhibitors. In this regard, the effectiveness of these agents can be measured by standard enzyme kinetics assays known to those skilled in the art (e.g., the measurement of $V_{max}$, $K_M$ and the like). Of course, all of these techniques may be automated using, for example, microarray systems and robotics.

An example of screening small molecules for their effect on decreasing the ratio of Twist/Twist homodimerization to Twist/E heterodimerization comprises providing a library of small molecules to be screened for the ability decrease the ratio of Twist/Twist homodimerization to Twist/E heterodimerization and forming a reaction mixture comprising a small molecule to be screened for the ability to decrease the ratio of Twist/Twist homodimerization to Twist/E heterodimerization, and a mixture of Twist and E proteins; incubating the reaction mixture for a period of time and under conditions appropriate for the formation of Twist/Twist homodimers and Twist/E heterodimers; determining the ratio of homodimer to heterodimer following the incubation; comparing the ratio of homodimer to heterodimer determined to the ratio detected in an otherwise identical incubation mixture which does not include a small molecule to be screened for the ability to promote Twist/E heterodimerization and/or inhibit Twist/Twist homodimerization, a substantial change in the ratio determined to that of the otherwise identical incubation mixture being indicative of the small molecule being characterized by the ability to promote Twist/E heterodimerization and/or inhibit Twist/Twist homodimerization. One practiced in the art will realize that similar assays can be used to identify a small molecule characterized by the ability to inhibit Twist/Twist homodimerization or promote Twist/E heterodimerization.

Small molecule (combinatorial) chemical libraries are well known in the art. Numerous libraries are available to those skilled in the art and, with the teachings provided herein, one skilled in the art would be able to identify small molecule agents that function to decrease the ratio of Twist/Twist homodimers to Twist/E heterodimers. Additionally, the synthesis and screening of small molecule libraries (e.g., combinatorial chemical libraries) are well known in the art (See, for example, U.S. Pat. No. 6,060,596 to Lerner; U.S. Pat. No. 6,185,506 to Cramer, et al.; U.S. Pat. No. 6,377,895 to Horlbeck; U.S. Pat. No. 6,936,477 to Still, et al.; Shipps, et al., Proc. Natl. Acad. Sci. USA, 94:11833-11838, 1997; Stockwell, et al., Chemistry & Biology, 6:71-83, 1999, all of which are incorporated herein by reference). (See, also, for example, www.combichem.net; www.combichemistry.com; www.combinatorial.com and pubs.acs.org/journals/jcchff/).

In another embodiment, the agent is a molecule characterized by its ability to inhibit Twist expression and, thereby decrease the ratio of Twist/Twist homodimers to Twist/E heterodimers in the organism. Such agents may be, for example, small inhibitory RNAs (siRNA) or expression constructs to, for example, Twist. As is demonstrated in the cited patent references and other cited references below, the inhibition of gene translation by antisense technology is well known by those skilled in the art. Antisense inhibition of Twist and E protein can be accomplished using an antisense construct which encodes an RNA (an antisense RNA) which is complementary to a contiguous portion of either the Twist or E protein mRNA. Preferably the antisense RNA is between 20 nucleotides or up to the entire length of the mRNA. In a preferred embodiment, the antisense RNA is about 20-200 bases. The antisense RNA can be complementary to any isolated region of the Twist mRNA. In one embodiment, the antisense RNA is complementary to the 5' region of the Twist mRNA. In a related embodiment, the antisense RNA includes a region that is complementary to the translation start site. In a preferred embodiment, the complementary region encompasses the start site of translation and also encompasses upstream adjacent 5' untranslated sequence and downstream adjacent coding sequence. In any event, the identification of an effective antisense construct is measured by comparing, for example, the inhibition of Twist expression, the ratio of T/T and/or T/E dimers or measuring the downstream effect of the antisense construct (e.g., the effect on cell growth and/or mobility) as compared to, for example, similar cells not comprising the antisense construct or comprising an empty expression vector.

Antisense technology can also be accomplished using synthesized oligonucleotides, or functional equivalents thereof, as an inhibitor to disrupt the Twist gene expression. The oligonucleotide is either complementary to the Twist gene or the Twist mRNA and delivery of multiple copies of the oligonucleotide into a target cells inhibits Twist gene expression of the Twist in the cell at either the level of transcription or translation, respectively. Both oligonucleotides and antisense RNA used in the above method must be delivered into the cell in which partial or total inhibition of the Twist is desired. Many methods of delivery of nucleic acids into cells are well know in the art. Some examples include, without limitation, electroporation, microinjection, calcium phosphate transfection, cellular import signal peptide mediated delivery, receptor mediated uptake, and liposome mediated delivery. The particular method of delivery of the nucleic acid into the cell depends upon the circumstances of the individual cell (e.g., the cell type, the environment of the cell, the amount of inhibitor to be delivered) and can be determined by the skilled practitioner. The use of siRNAs for the control of gene expression is well known in the art (for example, see, U.S. Pat. Nos. 5,107,605 to Shewmaker, et al.; 5,457,189 to Crooke, et al., 6,566,501 to Amar, 6,610,663 to Cook, et al., 6,737,512 to Wu, et al. and U.S. Pat. No. 6,303,374 to Zhang, et al., all of which are incorporated herein by reference). Therefore, one skilled in the art would be able to practice this aspect of the present invention without undue experimentation.

The exogenous expression of E protein will decrease the ratio of Twist/Twist homodimers to Twist/E protein heterodimers. The production of expression constructs is well known in the art. An expression construct encoding E protein may be transfected into cells as described above for the transfection of antisense siRNA.

The decrease in the ratio of Twist/Twist homodimers to Twist/E protein heterodimers can also be achieved by developing modified versions of both Twist protein and E protein. Said modifications may be developed through protein engineering or via the process of directed molecular evolution. In either instance, rather than alter the ratio of Twist/Twist homodimers to Twist/E heterodimers, proteins are selected that are able to promote or inhibit the formation or function of native T/T homodimers or T/E heterodimers, depending on what result is desired. Nucleotides encoding said modified proteins are transfected into target cells at a number that would allow the exogenous protein to out compete the native protein thus resulting in the formation of dimers comprising the modified protein and with modified function. In this way, modulation of cell growth would be achieved via the change in effectiveness of the dimers formed (i.e., even though the ratio of T/T to T/E dimers may or may not change over non-transfected cells or cells transfected with an empty construct, the function of the dimers present would have been modified) rather than or in addition to a change in the ratio of dimers present. Examples of directed molecular evolution can be found in the art. Examples include U.S. Pat. No. 5,605,793 to Stemmer, et al., or U.S. Pat. No. 6,537,776 to Short, which are included herein by reference. The proteins generated by directed molecular evolution will have a lesser, greater or equal ability to interact with Twist or E protein than the native peptides.

Small molecules may also affect Twist activity by modulating the function of Twist pathway components that are located downstream of Twist. Although the present invention is not limited to any particular mechanism, it is believed that the T/T homodimers induce periostin gene expression while T/E heterodimers inhibit periostin and induce thrombospondin (TSP-1) expression (See, e.g., FIG. 13). Perostin is a secreted protein that induces cell migration and promotes angiogenesis and tumor metastatis growth (Bao, S., et al., Cancer Cell, 5:329-339, 2004). Conversely, TSP-1 is a potent inhibitor of endothelial migration and angiogenesis and is downregulated in many tumors (Iruela-Arispe, M. L., et al., Int J Biochem Cell Biol, 36:1070-1078, 2004) and mesenchymal cells (Hayashido, et al., Int J Mol Med., 12:447-452, 2003). Consequently, Twist positively or negatively affects tumor cell behavior dependent upon which Twist dimer is prevalent. In this regard, agents that modulated Twist or E protein modulated cell growth and mobility through downstream effectors such as perostin or TSP-1 are contemplated to be part of the present invention.

Twist Involvement in Mesenchymal Cell Growth

In another aspect, the present invention contemplates a method for promoting bone formation in an organism, the method comprising contacting the cells with an agent characterized by the ability to increase the ratio of Twist/Twist homodimers to the ratio of Twist/E heterodimers in the organism. The increase of the ratio of Twist/Twist homodimers to Twist/E heterodimers can be used in therapies for the treatment of abnormalities wherein there is a reduction in the growth of cells of mesenchymal origin, for example, craniofacial abnormalities (e.g., cleft palate, cleft face), broken bones and limb abnormalities. In a preferred embodiment, the organism to be treated by way of an increase in the ratio of Twist/Twist homodimers to Twist/E heterodimers requires the promotion of, for example, bone growth. In a more preferred embodiment, the cells contacted with the agent comprise, for example, osteoblasts, osteocytes, oesteoclasts, chondrocytes myoblasts and other muscle cell types. In a preferred embodiment, the organism is a mammal. In a more preferred embodiment, the organism is a human. The agent used to contact the cells can be any agent that is effective in increasing the ratio of Twist/Twist homodimers to Twist/E heterodimers. Such agents can be administered to the organism by techniques known in the art including, but not limited to, injection (e.g., injection directly into a bone of joint, subcutaneous, intramuscular, vascular, etc.) wherein they type of injection is determined by the type of therapy required (e.g., vascular injections may be preferred for application of the agent to the entire body whereas injections into a joint, for example, may be required for application of the agent to a specific treatment site). Such agents can also be administered by infusion into, for example, the blood stream or the target organ or other target location. In other embodiments, the agents are administered orally. The agent may comprise other reagents to aid in the administration, manufacture, storage and transport of the agent including, but not limited to, binders, stabilizers, colors, flavors, buffers, excipients, etc. The organism that is the recipient of the agent can then be monitored for the increase in the ratio of Twist/Twist to Twist/E dimers. Samples for monitoring may be acquired by blood draws, biopsies, etc. The detection of the increase in the ratio of Twist/Twist to Twist/E dimers can be detected by, for example, SDS-PAGE gel electrophoresis, Western blotting, or other immunohistochemical techniques (e.g., ELISA, RIA or FACS assays) or other suitable assays known in the art.

In one embodiment, the agent is a small molecule characterized by the ability to increase the ratio of Twist/Twist homodimers to Twist/E heterodimers by inhibiting Twist/E heterodimerization or by promoting Twist/Twist homodimerization. The agent(s) to be administered to the organism can be selected from, for example, small molecule libraries (e.g., combinatorial chemical libraries). Such libraries are known in the art and are commercially available.

Techniques are known to those skilled in the art for the selection of agents from such libraries. In the present embodiment, the agent is being screened for its ability to increase the ratio of Twist/Twist homodimers to Twist/E heterodimers either by inhibiting Twist/E heterodimerization or by promoting Twist/Twist homodimerization. The present invention is not limited by the nature of the screening method. For example, in certain embodiments, the present invention contemplates screening methods wherein Twist and/or E protein is bound to a solid surface, test agents are contacted to the Twist and/or E protein and agents that bind to the Twist and/or E proteins are detected. Such detection may utilize, for example, immunological methods, radiolabeling of the test agents, fluorescent or other tags (e.g., streptavidin or myc-tagged labeled molecules), etc. Examples of using tagged molecules to monitor Twist and E dimer formation are given in the Examples section. Additionally, the yeast two-hybrid system (Fields S, Song O. K. A novel genetic system to detect protein-protein interactions. *Nature* 340:245-6, 1989; incorporated herein by reference) can be used to agents that decrease the ratio of Twist/Twist homodimers to Twist and E heterodimers. In other embodiments, the assay is performed in solution. In other assays, for example, the agent suspected of increasing the ratio of Twist/Twist homodimers to Twist/E heterodimers is added to a mixture of Twist and E protein and dimer formation is compared to a control mixture without the test agent added. Additionally, the identification and effectiveness of the agents may be determined by comparing, for example, by the downstream effect of the agent (e.g., the effect on cell growth and/or mobility) as compared to, for example, similar cells not exposed to the test agent or similar cells comprising another suitable control. Effective agents may work, for example, by binding to Twist or E protein as competitive or non-competitive inhibitors. In this regard, the effectiveness of these agents can be measured by standard enzyme kinetics assays known to those skilled in the art (e.g., the measurement of $V_{max}$, $K_M$ and the like). Of course, all of these techniques may be automated using, for example, microarray systems and robotics.

An example of screening small molecules for their effect on increasing the ratio of Twist/Twist homodimerization to Twist/E heterodimerization comprises providing a library of small molecules to be screened for the ability increase the ratio of Twist/Twist homodimerization to Twist/E heterodimerization and forming a reaction mixture comprising a small molecule to be screened for the ability to increase the ratio of Twist/Twist homodimerization to Twist/E heterodimerization, and a mixture of Twist and E proteins; incubating the reaction mixture for a period of time and under conditions appropriate for the formation of Twist/Twist homodimers and Twist/E heterodimers; determining the ratio of homodimer to heterodimer following the incubation; comparing the ratio of homodimer to heterodimer determined to the ratio detected in an otherwise identical incubation mixture which does not include a small molecule to be screened for the ability to inhibit Twist/E heterodimerization and/or promote Twist/Twist homodimerization, a substantial change in the ratio determined to that of the otherwise identical incubation mixture being indicative of the small molecule being characterized by the ability to either inhibit Twist/E heterodimerization and/or promote Twist/E. One practiced in the art will realize that similar assays can be used to identify a small molecule characterized by the ability to promote Twist/Twist homodimerization or inhibit Twist/E heterodimerization.

Small molecule (combinatorial) chemical libraries are well known in the art. Numerous libraries are available to those skilled in the art and, with the teachings provided herein, one skilled in the art would be able to identify small molecule agents that function to decrease the ratio of Twist/Twist homodimers to Twist/E heterodimers. Additionally, the synthesis and screening of small molecule libraries (e.g., combinatorial chemical libraries) are well known in the art (See, for example, U.S. Pat. No. 6,060,596 to Lerner; U.S. Pat. No. 6,185,506 to Cramer, et al.; U.S. Pat. No. 6,377,895 to Horlbeck; U.S. Pat. No. 6,936,477 to Still, et al.; Shipps, et al., Proc. Natl. Acad. Sci. USA, 94:11833-11838, 1997; Stockwell, et al., Chemistry & Biology, 6:71-83, 1999, all of which are incorporated herein by reference). (See, also, for example, www.combichem.net; www.combichemistry.com; www.combinatorial.com and pubs.acs.org/journals/jcchff/).

In another embodiment, the agent is a molecule characterized by its ability to inhibit E protein expression and, thereby increase the ratio of Twist/Twist homodimers to Twist/E heterodimers in the organism. Such agents may be, for example, small inhibitory RNAs (siRNA) or expression constructs to, for example, E protein. As is demonstrated in the cited patent references and other cited references below, the inhibition of gene translation by antisense technology is well known by those skilled in the art. Antisense inhibition of Twist and E protein can be accomplished using an antisense construct which encodes an RNA (an antisense RNA) which is complementary to a contiguous portion of either the Twist or E protein mRNA. Preferably the antisense RNA is between 20 nucleotides or up to the entire length of the mRNA. In a preferred embodiment, the antisense RNA is about 20-200 bases. The antisense RNA can be complementary to any isolated region of the E protein mRNA. In one embodiment, the antisense RNA is complementary to the 5' region of the E protein mRNA. In a related embodiment, the antisense RNA includes a region that is complementary to the translation start site. In a preferred embodiment, the complementary region encompasses the start site of translation and also encompasses upstream adjacent 5' untranslated sequence and downstream adjacent coding sequence. In any event, the identification of an effective antisense construct is measured by comparing, for example, the inhibition of E protein expression, the ratio of T/T and/or T/E dimers or measuring the downstream effect of the antisense construct (e.g., the effect on cell growth and/or mobility) as compared to, for example, similar cells not comprising the antisense construct or comprising an empty expression vector.

Antisense technology can also be accomplished using synthesized oligonucleotides, or functional equivalents thereof, as an inhibitor to disrupt the E protein gene expression. The oligonucleotide is either complementary to the E protein gene or the E protein mRNA and delivery of multiple copies of the oligonucleotide into a target cells inhibits E protein gene expression of the E protein in the cell at either the level of transcription or translation, respectively. Both oligonucleotides and antisense RNA used in the above method must be delivered into the cell in which partial or total inhibition of the E protein is desired. Many methods of delivery of nucleic acids into cells are well know in the art. Some examples include, without limitation, electroporation, microinjection, calcium phosphate transfection, cellular import signal peptide mediated delivery, receptor mediated uptake, and liposome mediated delivery. The particular method of delivery of the nucleic acid into the cell depends upon the circumstances of the individual cell (e.g., the cell type, the environment of the cell, the amount of inhibitor to be delivered) and can be determined by the skilled practitioner. The use of siRNAs for the control of gene expression is well known in the art (for example, see, U.S. Pat. Nos. 5,107,605 to Shewmaker, et al.; 5,457,189 to Crooke, et al., 6,566,501 to Amar, 6,610,663 to Cook, et al., 6,737,512 to Wu, et al. and U.S. Pat. No. 6,303,374 to Zhang, et al., all of which are incorporated herein by reference). Therefore, one skilled in the art would be able to practice this aspect of the present invention without undue experimentation.

The exogenous expression of Twist will increase the ratio of Twist/Twist homodimers to Twist/E protein heterodimers. The production of expression constructs is well known in the art. An expression construct encoding Twist may be transfected into cells as described above for the transfection of antisense siRNA.

In another aspect, the present invention contemplates a method for inhibiting bone formation (e.g., excessive bone formation such as that found in craniosynostosis) in an organism, the method comprising contacting the cells with an agent characterized by the ability to decrease the ratio of Twist/Twist homodimers to the ratio of Twist/E heterodimers in the organism. The compositions and methods for the inhibition of mesenchymal cell growth are similar to those compositions and methods for the inhibition of metastatic cell growth given above, where the reader is referred, except for diseases treated and locations of administration, as follows.

The decrease of the ratio of Twist/Twist homodimers to Twist/E heterodimers can be used in therapies for the treatment of abnormalities wherein there is an increase of the growth of cells of mesenchymal origin, for example, craniofacial abnormalities (e.g., craniosynostosis), limb abnormalities, etc. In a preferred embodiment, the organism that needs a decrease in the ratio of Twist/Twist homodimers to Twist/E heterodimers requires the inhibition of mesenchymal (e.g., bone) cell growth. In a more preferred embodiment, the cells contacted with the agent comprise, for example, osteoblasts, osteocytes, oesteoclasts and chondrocytes. In a preferred embodiment, the organism is a mammal. In a more preferred embodiment, the organism is a human. The agent used to contact the cells can be any agent that is effective in decreasing the ratio of Twist/Twist homodimers to Twist/E heterodimers. Such agents can be administered to the organism by techniques known in the art including, but not limited to, injection (e.g., injection directly into a bone of joint, subcutaneous, intramuscular, vascular, etc.) wherein they type of injection is determined by the type of therapy required (e.g., vascular injections may be preferred for application of the agent to the entire body whereas injections into a joint, for example, may be required for application of the agent to a specific treatment site). Such agents can also be administered by infusion into, for example, the blood stream or the target organ or other target location. In other embodiments, the agents are administered orally. The agent may comprise other reagents to aid in the administration, manufacture, storage and transport of the agent including, but not limited to, binders, stabilizers, colors, flavors, buffers, excipients, etc. The organism that is the recipient of the agent can then be monitored for the decrease in the ratio of Twist/Twist to Twist/E dimers. Samples for monitoring may be acquired by blood draws, biopsies, etc. The detection of the decrease in the ratio of Twist/Twist to Twist/E dimers can be detected by, for example, SDS-PAGE gel electrophoresis, Western blotting, or other immunohistochemical techniques (e.g., ELISA, RIA or FACS assays) or other suitable assays known in the art.

In another aspect, the present invention contemplates a method for modulating the rate of growth of mesenchymal cells in an organism, the method comprising contacting the cells with an agent characterized by the ability to alter the ratio of Twist/Twist homodimers to the ratio of Twist/E heterodimers in the organism. The modulation of mesenchymal cell growth can be used in therapies for the treatment of abnormalities, diseases and injuries associated with cells and tissues derived from cells of mesenchymal origin, for example, wound healing, wasting diseases and muscular dystrophies etc. The compositions and methods for the modulation of mesenchymal cell growth are similar to those compositions and methods for the inhibition and promotion of bone formation given above, where the reader is referred. One skilled in the art will recognize that the administration of agents characterized by the ability to alter the ratios of Twist/Twist homodimers and Twist/E heterodimers is within the skill of one practiced in the art. For example, and as given above, the organism that requires the altering of the ratios of Twist/Twist homodimers and Twist/E heterodimers is, in a preferred embodiment, a mammal. In a more preferred embodiment, the organism is a human. The agent used to contact the mesenchymal cells can be any agent that is effective in altering the ratio of Twist/Twist homodimers to Twist/E heterodimers. Such agents can be administered to the organism by techniques known in the art including, but not limited to, injection (e.g., subcutaneous, intramuscular, vascular, etc.) wherein they type of injection is determined by the area to be treated. Such agents can also be administered by infusion into, for example, the blood stream or the target organ or other target location. In other embodiments, the agents are administered orally. The agent may comprise other reagents to aid in the administration, manufacture, storage and transport of the agent including, but not limited to, binders, stabilizers, colors, flavors, buffers, excipients, etc. The organism that is the recipient of the agent can then be monitored for any altering of the ratio of Twist/Twist to Twist/E dimers. Samples for monitoring may be acquired by blood draws, biopsies, etc. The detection of the altering of the ratio of Twist/Twist to Twist/E dimers can be detected by, for example, SDS-PAGE gel electrophoresis, Western blotting, or other immunohistochemical techniques (e.g., ELISA, RIA or FACS assays) or other suitable assays known in the art.

In one embodiment, the agent is a small molecule characterized by the ability to altering the ratio of Twist/Twist homodimers to Twist/E heterodimers by promoting or inhibiting Twist/E heterodimerization or by promoting or inhibiting Twist/Twist homodimerization. The agent(s) to be administered to the organism can be selected from, for example, small molecule libraries (e.g., combinatorial chemical libraries). In another embodiment, the small molecule (for example an siRNA) is characterized by the ability to inhibit Twist expression. In another embodiment, the small molecule (for example an siRNA) is characterized by the ability to inhibit E protein expression. In yet another embodiment, the agent is an expression construct encoding either Twist or E protein. One skilled in the art will be able to apply the invention, as described above to the identification and application of small molecules for altering the ratio of Twist/Twist to Twist/E in the mesenchymal cells of an organism.

Twist Involvement in Mesenchymal Cell Growth

Craniosynostosis is a fairly common disorder occurring in about 1 in 2500 individuals. Non-syndromic craniosynostosis is most common, however 20% of all cases are associated with mutations in the gene TWIST or one of the fibroblast growth factor receptor (FGFR) genes. TWIST haploinsufficiency is associated with Saethre-Chotzen syndrome, which is the most common autosomal dominant disorder of craniosynostosis (el Ghouzzi, et al., *Nat Genet* 15:42-6, 1997; Howard, et al., *Nat Genet* 15:36-41, 1997). More than 50 different mutations have been identified in the TWIST gene and are predicted to cause loss of function (Gripp, et al., *Hum Mutat* 15:479, 2000), which is also indicated by Twist +/− mice presenting a similar phenotype (Bourgeois et al., *Hum Mol Genet* 7:945-957, 1998; Carver, et al., *Anat Rec* 268:90-92, 2002; el Ghouzzi, et al., *Nat Genet* 15:42-46, 1997). Conversely, a family has been identified with trisomy at the TWIST locus resulting in cranium bifidum, which is characterized by a persistent calvarial foramen and open sutures (Stankiewicz, et al., *Am J Med Genet* 103:56-62, 2001). These two opposing clinical phenotypes resulting from either half or one and a half times the normal amount of Twist, respectively, illustrate the critical requirement for the tight regulation of Twist expression.

It is discussed herein that Twist has both positive and negative functions regulating mesenchymal cell specification and differentiation. Twist was originally identified in *Drosophila* as a gene required for gastrulation and mesoderm formation, but also has a seemingly opposing but evolutionarily conserved function of inhibiting the differentiation of mesenchymal tissues, including muscle and bone (Castanon and Baylies, *Gene* 287, 11-22, 2002; O'Rourke and Tam, *Int J Dev Biol* 46, 401-13, 2002). The mechanisms underlying these disparate functions are unclear but may be dependent on the dimer partner of Twist. bHLH transcription factors are classified into different categories based on their tissue distribution, partner choice, DNA binding and structural properties. Twist falls into Class II, which contains tissue-specific bHLH proteins such as MyoD. These proteins form heterodimers with Class I bHLH proteins, termed E proteins, which are widely expressed in many tissues. Id proteins represent a third class of HLH proteins that lack the basic domain and therefore cannot bind DNA. These proteins preferentially dimerize with E proteins and disrupt functional Class I/II bHLH heterodimers from forming (Massari and Murre, *Mol Cell Biol* 20:429-440, 2000). The majority of Class II bHLH proteins do not form stable homodimers (Vinals, et al., *Embo J* 23:3527-3537, 2004; Vinals and Ventura, *J Biol Chem* 279: 45766-45772, 2004), however studies in *Drosophila* suggest that homodimers of Twist mediate mesoderm formation (Castanon, et al., *Development* 128:3145-3159, 2001). Therefore, Twist may uniquely form functional heterodimers (T/E) and homodimers (T/T) that may have different activities and may account for the opposing actions ascribed to Twist. The ratio of T/T to T/E within a cell would therefore determine the functional output of Twist expression.

The cranial sutures are the growth centers separating the bones of the skull and are composed of two opposing osteogenic fronts and an intervening mesenchyme. Twist is expressed throughout the suture mesenchyme and osteogenic fronts, while Id expression is confined to the osteogenic fronts (Johnson, et al., *Mech Dev* 91:341-345, 2000; Rice, et al., *Development* 127:1845-1855, 2000). E2A (E12 and E47) and HEB E proteins are expressed throughout the suture and in differentiating osteoblasts (Funato, et al., *Mol Cell Biol* 21:7416-7428, 2001). In was determined that Id competes with Twist for dimerization with E proteins in the osteogenic fronts, forcing Twist to form homodimers, while in the intervening suture mesenchyme, where Id is absent, Twist forms T/E heterodimers. These dimers then differentially regulate gene expression and cell behavior in these areas. The data herein support this and indicate that there is dynamic regulation of Twist dimer formation in the cranial sutures that is altered in Twist +/− mice. Twist haploinsufficiency increases the ratio of T/T to T/E, which promotes suture fusion, and increasing T/E formation in the sutures of these mice prevents fusion.

Twist Involvement in Metastatic Cell Growth

Recent findings as presented in the Examples section of this application) provide a mechanistic understanding of Twist function, which can be utilized as a target to regulate cell behavior. In efforts to better characterize the molecular basis of Twist function, and as embodied in the present invention, it has recently found that the activity of Twist depends on its dimer partner. Unlike most other bHLH proteins, Twist can form functional homodimers (T/T) as well as heterodimers with ubiquitously expressed bHLH E proteins (T/E). It was found that T/T dimers and T/E dimers have distinct activities, regulating the expression of different sets of genes and have opposing effects on cell proliferation and migration.

Metastasis involves several steps including invasion of the tumor into surrounding tissues, intravasation from the tumor into the vasculature, survival in the vasculature, extravation into target tissues and growth at the ectopic site. As detailed in the Example section, infra, this work shows that Twist dimers differentially affect these stages of tumor progression. Breast and prostate cancers are among the most common of human cancers, affecting 1 in 8 women and 1 in 6 men, respectively. Tumor metastasis is the major cause of death from these and many other cancers leading to several hundred thousand deaths each year in the United States alone. While advancements have been made in the diagnosis and treatment of these and other cancers, more progress needs to be made. The present invention provides tools and methods for the treatment of metastatic cancers and for the screening of agents for the treatment of metastatic cancers via the modulation of T/T and T/E formation.

As stated above, different forms of Twist complexes have opposing effects on tumor progression. This data shows that T/T dimers promote tumor invasion and metastasis, while T/E dimers inhibit these. Therefore, the level of Twist expression may be less important than the ratio of Twist to Id expression, which would determine which dimer is formed. Discussed in connection with the cranial sutures of Twist +/− mice, where T/T dimers predominate and promote premature suture fusion, the promotion of T/E formation can change cell behavior and in the case of the cranial sutures can prevent suture closure. Promotion of T/E formation in breast tumors similarly changes cell behavior and inhibit tumor progression. Therefore, in one embodiment of the present invention, Twist dimerization is a fruitful target for therapeutics to inhibit metastasis. Furthermore, the identification of genes regulated by T/T dimers (e.g., periostin expression, see, infra) may represent useful diagnostic indicators of the metastatic potential of a tumor.

Figure 9:
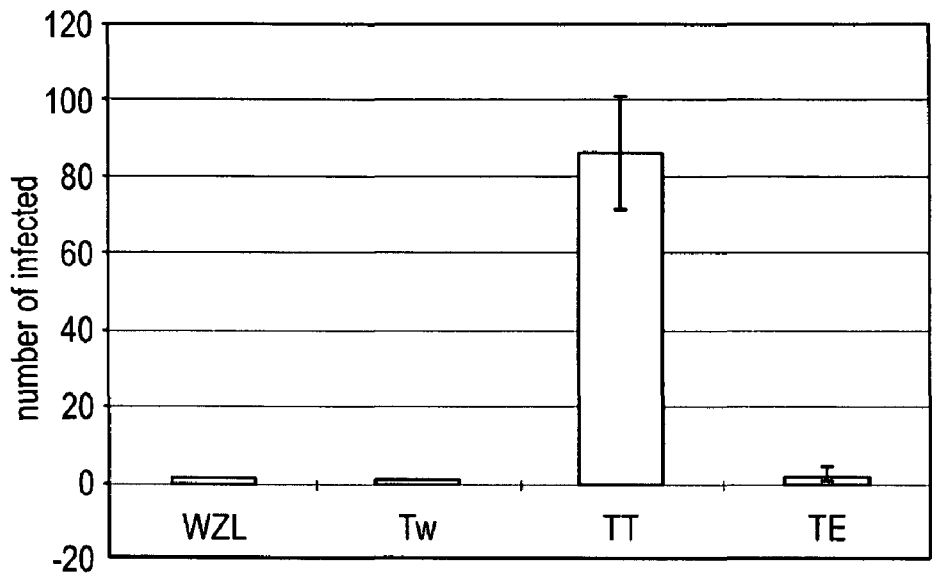
FIG. 9 shows 2000 C3H10T1/2 cells infected with a control retrovirus (WZL) or with one expressing TWIST (Tw), TT (TT), or TE (TE) were plated in soft agar and allowed to grow for 2 weeks in the presence of 10% FBS and 10 ng/ml FGF1. Cells were stained with 0.005% crystal violet and colonies were counted.

One widely used transgenic model of mammary tumorigenesis expresses the oncoprotein, polyoma middle T antigen (PyVT) under the control of the mouse mammary tumor virus (MMTV) LTR, which restricts expression to the mammary epithelium (Lin, et al., Am. J. Pathol, 163:2113-2126, 2003). In this model mammary hyperplasia can be detected as early as 4 weeks and 100% of these mice develop carcinoma, the vast majority by 14 weeks. This progression occurs in four distinct identifiable stages from hyperplasia to malignant and is comparable to the human disease progression classified as benign to invasive carcinoma. This model also mimics tumorigenesis induced by ErbB2/neu overexpression, which is amplified in 25% of human breast cancer, as both activate the ras and PI3 kinase pathways. Interestingly, Twist cooperates with ras to promote aspects of cellular transformation such as anchorage-independent growth (Maestro, et al., Genes Dev. 13:2007-2217, 1999). This activity of Twist is mediated by T/T dimers. Embryonal fibroblasts expressing T/T were able to grow in soft agar in the presence of FGF, which activates ras (FIG. 9). Therefore promotion of T/T dimers is able to cooperate with PyVT to promote breast tumor progression.

Thus, T/T dimers promote tumor progression while T/E dimers inhibit this process showing that Twist dimerization is a fruitful therapeutic target to regulate metastatic growth. The identification of genes that are differentially regulated by T/T and T/E are also useful diagnostic indicators of metastatic potential.

Twist Function

Although the present invention is not limited to any particular mechanism, it is believed that cell growth and cell mobility (and, in its most aberrant sense, metastasis) is regulated in a large part by the ratio of T/T to T/E dimers. In this regard, T/T dimes are believed to function as transcription factors that are responsible for the synthesis of agents directly or indirectly related to the promotion of cell growth, and cell mobility. Interestingly and by way of example, several of the genes that have been found to be regulated by the two dimers have either positive or negative effects on tumorigenesis. Twist homodimers induce periostin gene expression while T/E dimers inhibit periostin and induce thrombospondin (TSP-1) expression. Periostin is a secreted protein that induces cell migration and promotes angiogenesis and tumor metastatic growth (Sigvardsson, M., et al., Immunity 7:25-36, 1997). Conversely, TSP-1 is a potent inhibitor of endothelial migration and angiogenesis and is downregulated in many tumors (Bakiri, L., et al., Mol Cell Biol, 22:4952-4964, 2002). Consequently, Twist may positively or negatively affect cell growth and mobility (e.g., tumorigenesis) dependent on which dimer is present. E protein modulates the formation of T/T dimers by sequestering free Twist. When bound to E protein, Twist is no longer free to form homodimers. The modulation of either Twist or E protein, therefore, is critical to the control of the formation of T/T dimers and, thus, is critical to the control of cell growth, mobility and metastasis. The formation of T/T dimers can, therefore, be regulated by either modulating the total amount of either Twist or E protein in the cell or through the modulation of both peptides. In some aspects of the present invention, the ratio of T/T to T/E is decreased thereby slowing or inhibiting the fate of cell growth and cell mobility. In other aspects of the present invention, the ratio of T/T to T/E is increased thereby increasing the rate of cell growth and cell mobility.

EXAMPLES

Materials and Methods

Plasmids and Viral Constructs

CS2-mTwist and CSA-E12 were previously described (Spicer et al., Science 27:1476-1480, 1996). The tethered dimers were constructed as follows: For mTwist, KpnI and EcoRI sites were generated at the 3' end removing the stop codon. For E12 (E protein 12), an EcoRI site was generated in front of the initiation codon. A double-stranded oligonucleotide linker encoding the polypeptide tether (GGT ACC GGC GGA GGC TCG AGC GGT GGG AGC GGC GGA GGG TCC GGC GGA AGC TCG AGC GGT GGG AGC GGC GGA GGG TCC GGC GAA TTC) [SEQ ID NO.: 1] was inserted into KpnI-EcoRI-linearized pCS2mycTwist-E12 or pCS2mycTwist-Twist vector. To construct the T, TT and TE retrovirus vectors, the corresponding cDNA were excised and ligated into the pWZL-hygro vector (Serrano et al., Cell 88:593-602, 1997). Twist and E12 adenovirus were prepared by employing the Cre-lox recombination system as described previously (Hardy et al., J Virol 71:1842-1849, 1997) at a titer of ~$10^{12}$ viral particles/ml.

Electrophoretic Mobility Shift Assays

EMSA analysis was performed using in vitro-translated proteins and double-stranded oligos containing the E box binding site from the muscle creatine kinase (MCK) enhancer as a probe as previously described (Lassar et al., Cell 66:305-315, 1991).

Cell Culture and Gene Transfer

C3H10T1/2 cells (10T1/2) and 293T HEK cells (ATCC) were cultured in DMEM supplemented with 10% fetal bovine serum and penicillin-streptomycin. 293T HEK cells were transfected with CS2-(myc)Twist, CS2-(myc)Id1 and CSA-E12 expression constructs as previously described (Spicer et al., Science 272:1476-1480, 1996). Retroviral supernatants were prepared using transient transfection into the BOSC23 packaging cell line and 10T1/2 cells were infected as previously described (Novitch et al., Curr Biol 9:449-59, 1999).

To prepare primary osteoblasts, calvaria from P1 pups were cleaned from associated tissues and cut in half. Fragments were washed with 4 mM EDTA three times, followed by three washes in PBS and then digested in collagenase solution (Worthington Collagenase Type 2 at 317 u/mg) shaking for 10 minutes at 37° C. Digestions were repeated five times and digestions 3, 4, and 5 were pooled. Cells were filtered through mesh to remove any pieces of bone, and resuspended in α-MEM 10% FCS. Calvaria cells were differentiated in the same medium containing 10 mg/ml L-ascorbic acid, 500 mM β-glycerol phosphate. For adenoviral transduction, cells were incubated in serum-free medium with $10^3$ viral particles/cell in the presence of poly-D-lysine (Sigma) ($5 \times 10^3$ molecules/viral particle) for 2 h at 37° C., after which the medium was replaced with α-MEM 10% FCS.

Western Blotting

Western blot analysis was performed as previously described (Leshem et al., J Cell Physiol 184:101-9, 2000). Samples run in non-reducing conditions contained no β-mercaptoethanol and were not heated before loading. The following primary antibodies were used: monoclonal anti-β actin (1:1000 Sigma); monoclonal anti-TSP1 (Ab-11; 1:750, NeoMarker); rabbit polyclonal anti-Periostin (1:1000); rabbit polyclonal anti-E2a (sc-349, 1:1000, Santa Cruz Biotechnology); anti-phospho Smad1, rabbit polyclonal anti-Ser465/467 antibody (1:1000, Cell Signaling Technology) and a rabbit polyclonal antibody against total Smad1 (MADP1, 1:1000 Upstate Cell Signaling Solutions).

Immunostaining

10T1/2 cells were analyzed by immunofluorescence as previously described (Leshem et al., J Cell Physiol 184:101-9, 2000) using monoclonal anti-TSP1 (Ab-1; 1:250, NeoMarker). Images were obtained using confocal fluorescence microscopy. Paraffin sections of coronal and sagittal sutures of P1 pups were probed with anti-Twist rabbit polyclonal Ab (Santa Cruz, H-81) and anti-Id rabbit polyclonal Ab (Santa Cruz, Z-8; note this antibody recognizes all four Id proteins), followed by Tyramide signal amplification (TSA Biotin System, Perkin Elmer) and Vectastain Elite ABC kit (Vector Laboratories).

Heparin-Sepharose Affinity Chromatography

10T1/2 cell lines were plated at $5 \times 10^6$ cells per 15 cm dish with 20 ml of 0.2% FBS for 48 hours. Affinity chromatography was performed using CL-6B Heparin-Sepharose columns (Amersham Pharmacia Biotech). The column was equilibrated with 50 mM Tris-HCl buffer, pH 7.4, containing 10 mM EDTA. Conditioned media was applied to the column and the bound material was eluted with 1.5 M NaCl. Fractions were collected and concentrated using YM-10 centricons (Millipore), then assayed for TSP1 by western blot analysis.

Reverse-Transcription-Polymerase Chain Reaction

Total cellular RNA was isolated from cultures using Tri-reagent (Sigma) as previous described (Leshem et al., J Cell Physiol 184:101-9, 2000). The following mouse primer sets (5'-3') and annealing temperature were used for each particular complementary DNA (cDNA) amplification:

```
Id1
GGTGGATCCACCATG AAGGTCGCCAGTG,     [SEQ ID NO: 2]

TGGATCCGTCCATCTGGTCCCTCAGTGC;     [SEQ ID NO: 3]
```

```
Id3
AGGCGCTGAGCCCGGTGC,              [SEQ ID NO: 4]

CGGGAGGTGCCAGGACG                [SEQ ID NO: 5]
                                 (60° C.);

FGFR2
CTGTGCCGAATGAAGAACACGACC;        [SEQ ID NO: 6]

CAAAGTCTGCTATCTTCATCAC;          [SEQ ID NO: 7]

FGFR1
AAGGACAAACCCAACCGTGTGACC;        [SEQ ID NO: 8]

CAAAGTCTGCTATCTTCATCAC           [SEQ ID NO: 9]
                                 (55° C.);

Noggin
CGGCCAGCACTATCTACACA;            [SEQ ID NO: 10]

GTCTGTGACCACAGCCACAT             [SEQ ID NO: 11]
                                 (65° C.);

GAPDH
TGCGACTTCAACAGCAACTC;            [SEQ ID NO: 12]

GATGGAAATTGTGAGGGAGA             [SEQ ID NO: 13]
                                 (50° C).
```

Mice

Twist +/− and Wnt1-Cre mice were obtained from the Jackson Laboratory. A cre responsive transgene CAGCAT [SEQ ID NO.: 14]-Twist was constructed by replacing the lacZ region of CAG-CAT-Z (Araki et al., *Proc Natl Acad Sci, USA* 92:160-4, 1995) with the CS2 polylinker containing the murine Twist cDNA. This construct was used for microinjection to establish a transgenic line. Neural crest specific transgene expression was achieved by crossing the CAGCAT [SEQ ID NO.:14]-Twist mice with Wnt1-cre mice. Id1 −/−; Id3 +/− mice (Lyden et al., *Nature* 401:670-677, 1999) were crossed with the Twist +/− mice to obtain Twist +/− mice with varying numbers of functional Id alleles.

In Situ Hybridization

Skulls from newborn mice (P1) were fixed in 4% paraformaldehyde, cryosectioned and analyzed by in situ hybridization. In situ probes were against periostin, TSP-1 and FGFR2 as indicated. Wholemount in situ analysis was performed on P1 skulls following removal of the skin and brain. The in situ protocol was as in (Isaac et al., *Mech Dev* 93:41-8, 2000) with the modification that the skulls were digested with proteinase K digestion for 45 minutes. Section in situ analysis was performed on cryosections as in (Yoshida et al., *J Anat* 206: 437-44, 2005).

Calvarial Explants

Heads of P1 pups were de-skinned and sectioned horizontally below the nose. Calvaria were placed on Falcon cell culture inserts (PET pore size 0.4 µm) in six-well dishes containing DMEM:Ham's F-12K 50:50, 10 mg/ml L-ascorbic acid, 500 mM β-glycerol phosphate, 10% FBS, 1% penstrep. Explants were incubated in a CO2 incubator at 37° C. with media changed daily.

Example 1

Id Levels can Modulate Twist Dimer Composition

This Example shows that TWIST haploinsufficiency results in premature suture fusion. Saethre-Chotzen Syndrome is associated with haploinsufficiency of the bHLH transcription factor TWIST and is characterized by premature closure of the cranial sutures, termed craniosynostosis. In this Example we show that the activity of Twist is dependent on its dimer partner and these dimers differentially regulate gene expression and suture patency. We also show that the promotion of Twist heterodimer formation in the sutures of these mice prevents suture fusion. Therefore, we have provide a mechanistic understanding of craniosynostosis and have identified dimer partner selection as an important mediator of Twist function.

Activating mutations in FGFR2 or FGFR3 have been associated with at least two cases of Seathre-Chotzen Syndrome (Chun et al., *Am J Med Genet* 110:136-43, 2002; Paznekas et al., *Am J Hum Genet* 62:1370-80, 1998), indicating that activation of FGF signaling gives the same phenotype as TWIST haploinsufficiency. Consistent with this, FGFR2 expression extends into the mid-suture of Twist +/− mice while it is normally only expressed in the osteogenic fronts (Rice et al., *Development* 127:1845-1855, 2000). Since Twist is expressed in both the osteogenic fronts and in the mid-suture (Johnson et al., *Mech Dev* 91:341-5, 2000; Oshima et al., *J Cell Biochem* 86:792-804, 2002; Rice et al., *Development* 127:1845-1855, 2000), while Id1 is only in the osteogenic fronts (Rice et al., *Development* 127:1845-1855, 2000), it was suggested that Id inhibits Twist activity in the osteogenic fronts allowing FGFR2 to be expressed there.

Given that Id preferentially dimerizes with E proteins rather than class II HLH proteins like Twist (Be nezra et al., *Cell* 61:49-59, 1990), we have tested an alternative hypothesis, that Id expression promotes Twist homodimer formation in the osteogenic fronts and that the T/T and T/E dimers differentially regulate suture patency. In order to determine whether increasing Id levels would drive Twist to form T/T over T/E dimers, we developed a SDS-PAGE analysis where we could detect the Twist dimers that formed. 293T HEK cells were transfected with constructs expressing myc-tagged Twist, myc-tagged Id1, and E12 in different combinations and protein extracts were subjected to non-reducing SDS-PAGE gel followed by Western blot analysis without heating the samples before loading the gel (FIG. 1a, middle and right gels). When either Twist or E12 was transfected alone (lanes 2 and 3, respectively), two bands were detected in the non-reducing gels (middle and right) corresponding to the size of the monomers (T and E) and the respective homodimers (T/T and E/E). Co-transfection of Twist and E12 lead to a new band corresponding to the size of T/E heterodimers which was detected with both anti-myc and anti-E12 antibodies, along with the disappearance of the homodimer bands (lane 4, middle and right gels). Increasing amounts of Id1 protein caused the T/E band to decrease and a band corresponding to T/T homodimers to appear (lane 4-8, middle gel). o dimers were detected when extracts were heated before loading and run under reducing conditions (FIG. 1a, left gel). This data supports previous work indicating that Id preferentially interacts with E proteins (Benezra et al., *Cell* 61:49-59, 1990) and does not efficiently interact with Twist, which we have also confirmed using GST fusion and in vitro translated proteins. Therefore, Id levels determine the amount of free E protein that is available to dimerize with Twist and hence can determine which Twist dimer is formed.

Example 2

Forced Dimers of Twist are Less Sensitive to Competition by Other HLH Proteins

Figure 1B:
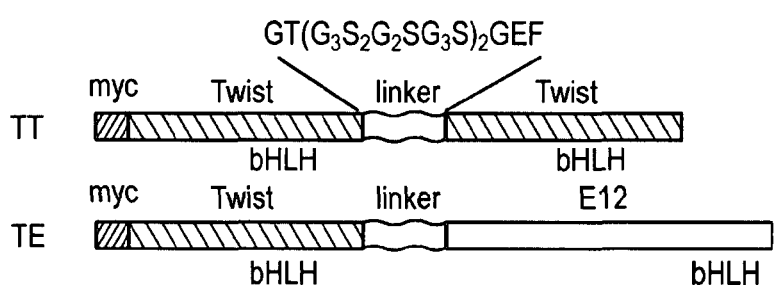
Figure 1C:
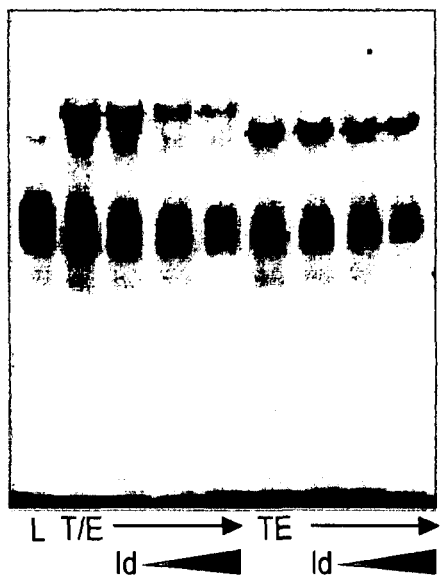
Figure 1D:
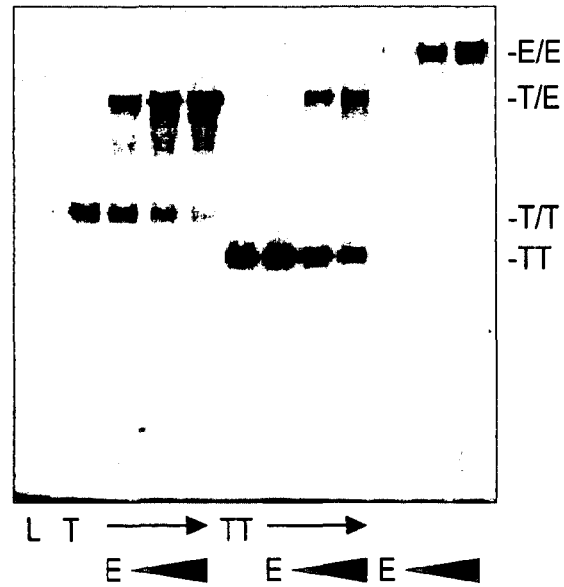

In order to determine if T/T homo- and T/E heterodimers have different activities we constructed "forced" dimers of Twist and E12 where the two monomers are linked by a flexible glycine-serine polylinker (FIG. 1b). This strategy was originally used with MyoD and the E protein E47 where it was shown that the tethered dimer was more resistant to inhibition by Id than the separate monomers (Neuhold and Wold, *Cell* 74:1033-42, 1993). The strategy has now been used successfully with several different transcription factors (Bakiri et al., *Mol Cell Biol* 22:4952-64, 2002; Castanon et al., *Development* 128:3145-59, 2001; Sigvardsson et al., *Immunity* 7:25-36, 1997). While we used E12 for our studies here, we have found no difference in the activity of Twist heterodimers composed of E12, E47 or HEB E proteins. To confirm that the tethered dimers could bind to a target binding sequence (E box) and were resistant to inhibition by other HLH proteins we performed an electrophoretic mobility shift assay (EMSA) comparing "forced" dimers to the separated monomers in their ability to bind an E box. Utilizing in vitro-translated proteins we found that both tethered dimers (TT and TE) formed specific complexes with the E box probe (FIGS. 1c and 1d). These complexes were slightly smaller than the complexes formed by the separated monomers (T/T and T/E) and this size difference is consistent with each of the separated monomers having myc epitope tags while only the amino-terminal partner of the tethered dimers has myc tags. As expected, the addition of increasing amounts of Id led to dissociation of the T/E monomer complex, while complex formation by the TE tethered dimer was not inhibited by Id (FIG. 1c). Similarly, addition of the E12 monomer quickly decreased the T/T homodimer complex with a commensurate increase in a T/E complex, and the TT tethered dimer complex was more resistant to dissociation by increasing levels of E12 (FIG. 1d). Thus both TT and TE tethered dimers can effectively bind E box-containing probes and their complexes with DNA are more stable when challenged by other HLH proteins.

Example 3

Twist Dimers Differentially Regulate Periostin and TSP-1 Gene Expression

Figure 2A:
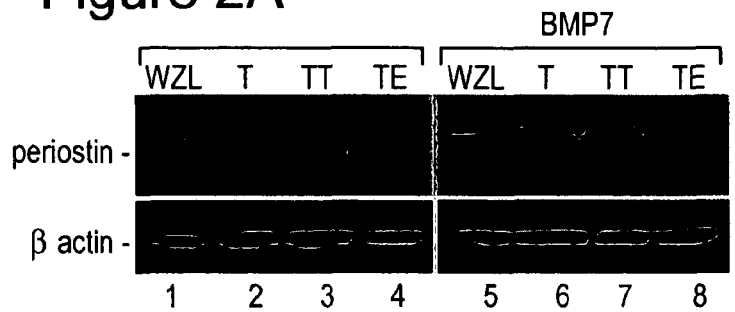
FIG. 2 shows Twist dimers differentially regulate gene expression (a-e) 10T1/2 cells were engineered to stably express Twist (T), the TT homodimer (TT) or the TE heterodimer (TE) by infection with pWZL retroviral constructs. Control 10T1/2 cells were infected with insertless pWZL virus (WZL). (a) TT enhanced periostin expression while TE cells inhibited it. The 10T1/2 cell lines were grown in 10% FBS without or with 100 ng/ml BMP7 for 4 days and then assayed for periostin and β-actin expression by western blot analysis. (b) Id1 is upregulated by BMP signaling. 10T1/2 cells were grown in 10% FBS without or with 100 ng/ml BMP7 for 4 days and then assayed for Id1, Id3, and GAPDH expression by RT-PCR. (c) TE induced Thrombospondin 1 (TSP-1) expression. 10T1/2 cell lines were grown in 10% FBS for 48 hours and then assayed for TSP-1 expression by immunofluorescence. (d) 10T1/2 cell lines were grown in 0.2% FBS for 48 hours and then the conditioned media was assayed for TSP-1 expression by western blot analysis following concentration on a heparin-sepharose column and elution with 1.5 M NaCl. (e) TT and TE dimers differentially regulate FGFR2 expression. 10T1/2 cell lines were grown without or with 100 ng/ml BMP7 for 4 days and were analyzed for FGFR1, FGFR2 and GAPDH expression by RT-PCR.
Figure 2B:
Figure 3A:
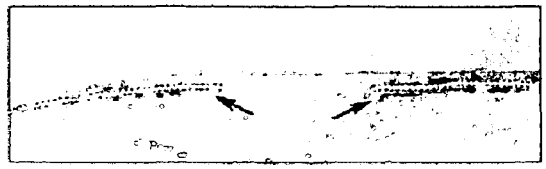
FIG. 3 shows Periostin and TSP-1 are expressed in the predicted T/T and T/E domains in the cranial sutures and are altered by changes in Twist expression. (a) Sections through the coronal and sagittal sutures of the skulls of P1 wild type and Twist +/– mice were analyzed for the indicated gene expression by in situ hybridization. Calvaria bones are outlined by dotted red lines. Note that in wild type sutures periostin expression does not extend to the end of the cranial bones but does in Twist +/– sutures. Expression of FGFR2 is increased and TSP-1 is decreased in the mid-suture of Twist +/– mice. (b) Skulls from wild type P1 mice were analyzed for periostin and TSP-1 expression by whole mount in situ hybridization. Note the decreased expression of TSP-1 in the coronal suture. C-coronal, F-frontal, S-sagittal. (c) Twist and Id protein expression in the sagittal and coronal sutures. Paraffin sections of sagittal and coronal sutures of wild type P1 mice were analyzed by immunohistochemistry for Twist and Id protein expression. Note that the Id antibody recognizes all Id proteins (Id1-4). (d) Wild type and Twist +/– P1 skulls were analyzed for TSP-1 expression in the sagittal suture. Note the decrease in staining in the Twist +/– skull. (e) Increased Twist expression in the osteogenic fronts induces TSP-1 expression. P1 skulls of CAGCAT [SEQ ID NO.: 14]-Twist and CAGCAT [SEQ ID NO.:14]-Twist/Wnt1-Cre mice were analyzed for TSP-1 expression.
Figure 3A:
Figure 3A:
Figure 3A:
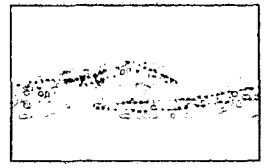
Figure 3A:
Figure 3A:
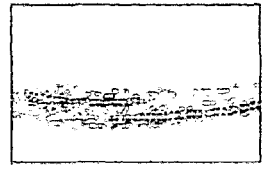
Figure 3A:
Figure 3A:
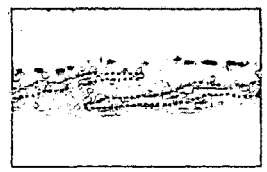
Figure 3A:
Figure 3A:
Figure 3A:
Figure 3A:
Figure 3A:
Figure 3A:
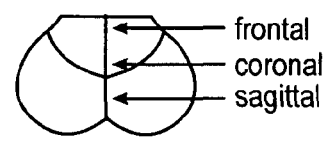
Figure 3A:
Figure 3A:

While Twist has been implicated in the regulation of cell specification and differentiation little is known about what genes Twist regulates to mediate these effects. We therefore wanted to determine if T/T and T/E dimers regulated different sets of genes. We also reasoned that the expression patterns of genes that are differentially regulated by the Twist dimers could be used to identify regions in the sutures where each dimer resides. We had previously performed microarray analysis comparing control C3H10T1/2 embryonal fibroblasts (10T1/2 cells) with ones over-expressing Twist. We had used 10T1/2 cells because they are a multipotential mesenchymal cell line able to undergo chondrogenesis and osteogenesis, but unlike primary calvarial cells the endogenous levels of Twist are very low allowing us to better determine the specific effects of the expression of different forms of Twist. We found that periostin, a member of the fasciclin I protein family, was significantly repressed by Twist and this data was confirmed by RT-PCR (data not shown) and western analysis (FIG. 3a). Interestingly, periostin was recently identified as a gene significantly induced by Twist in SAOS2 osteosarcoma cells (Oshima et al., *J Cell Biochem* 86:792-804, 2002). We reasoned that our differing results might be due to the different culture conditions favoring either Twist homodimers or heterodimers, which may differentially affect periostin expression. Indeed we found that 10T1/2 cells expressing TT enhanced periostin expression while expression of TE inhibited it (FIG. 2a). Cells expressing the Twist monomer more resembled TE-expressing cells and expressed less periostin. We next asked whether increasing Id levels in the Twist-expressing cells would promote more of a TT phenotype. BMPs induce Id1 expression in the calvarial sutures (Rice et al., *Development* 127:1845-1855, 2000) as well as in many cell lines including 10T1/2 cells (Ogata et al., *Proc Natl Acad Sci USA* 90:9219-22, 1993). We confirmed that BMP7 induced Id1 expression in 10T1/2 cells and found that Id3 expression was also slightly induced in these cells (FIG. 2b). Id2 and Id4 were not detected (data not shown). Consistent with our hypothesis, in the presence of BMP7 where Id levels were high, Twist induced periostin expression (FIG. 2a, compare lanes 2 and 6).

Figure 2C:
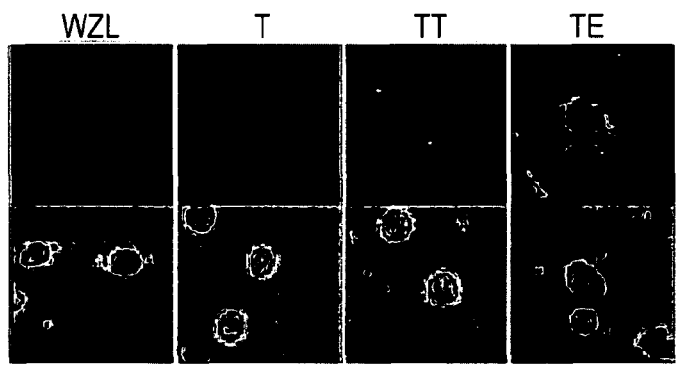
Figure 2D:

Recently, thrombospondin 1 (TSP-1) was shown to be upregulated in mesenchymal tissues of Id1 −/− mice (Volpert et al., *Cancer Cell* 2:473-83, 2002). Because Id does not directly regulate gene expression we hypothesized that there are more free E proteins available in the Id1 −/− mice, which may lead to increasing amounts of T/E dimers formed and these dimers may mediate the induction of TSP-1 expression. Consistent with this interpretation we found that TSP-1 expression was significantly induced in the 10T1/2 cells expressing TE (FIG. 2c). There was also significantly more TSP-1 in the conditioned media of TE-expressing cells than in control or TT cells and the Twist-expressing cells had an intermediate level of TSP-1 (FIG. 2d). Therefore, TT dimers induced periostin expression, while TE dimers inhibited periostin and induced TSP-1 expression. Furthermore, Twist cells behaved similar to TE cells under conditions where Id levels were low but acted like TT cells when Id levels were increased.

Example 4

Figures 3B, 3C:
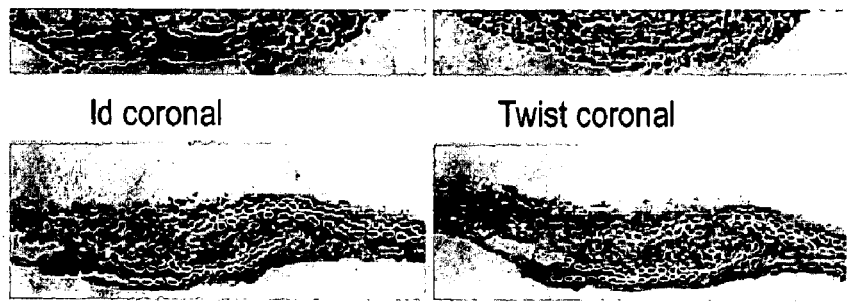

T/E and T/T Regulated Genes are Expressed in the Predicted Domains in the Cranial Sutures We next asked whether periostin and TSP-1 would be expressed in the predicted domains for T/T and T/E dimers in the cranial sutures based upon the expression patterns of Twist and Id1. Consistent with our hypothesis, we observed periostin expression in the osteogenic fronts while TSP-1 was expressed in the mid-suture area (FIG. 3a). Interestingly, TSP-1 was only significantly expressed in the sagittal and frontal sutures and not in the coronal suture, while periostin was expressed in all the sutures (FIGS. 3a and 3b), suggesting that the coronal suture may have a higher ratio of T/T to T/E. We therefore analyzed the expression patterns of Twist and Id proteins in the sagittal and coronal sutures to see if they would suggest a difference in dimer formation. Twist was similarly expressed throughout both sutures, however Id proteins were more extensively expressed in the coronal versus the sagittal suture (FIG. 3c). In the sagittal suture Id proteins were highly expressed in the osteogenic fronts with little or low expression in the mid-suture while in the coronal suture only a few cells in the mid-suture did not express Id. Consistent with an increase in T/T formation in this area there was only a small area in the mid-coronal suture that did not express periostin (FIG. 3a). We propose that this difference may be part of the reason that it is primarily the coronal suture that fuses due to TWIST haploinsufficiency (see below).

Example 5

Twist Dimers Differentially Regulate FGFR2 Expression

Figure 2E:
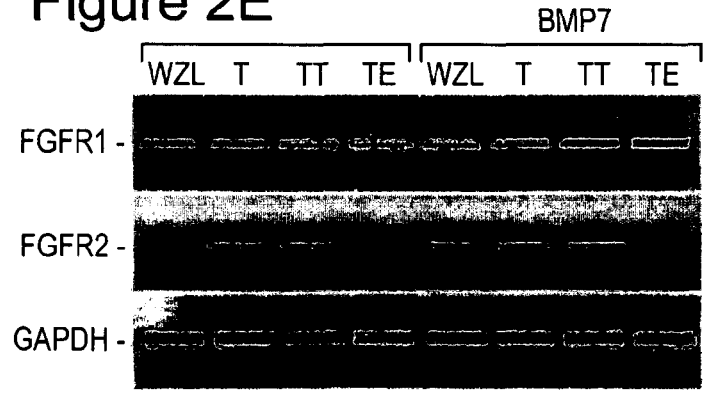

The expansion of FGFR2 expression into the mid-suture of Twist +/− mice (Rice et al., *Development* 127:1845-1855, 2000) could suggest that Twist normally represses FGFR2 expression. However, Twist induces FGFR expression during *Drosophila* gastrulation (Shishido et al., *Development* 117: 751-761, 1993), and this may be mediated by Twist homodimers (Castanon et al., *Development* 128:3145-59, 2001). We therefore examined our 10T1/2 cell lines to see if the Twist dimers differentially affected the expression of FGFR2. As can be seen in FIG. 2e, TT-expressing 10T1/2 cells induced FGFR2 expression while there was no expression in TE and control cells. Unlike the case with periostin and TSP-1 where the Twist-expressing cells behaved more similarly to the TE cells, FGFR2 was induced in the T cells similarly to the TT cells. Since there is most likely a mix of T/T and T/E dimers in the T cells, this suggests that genes are differentially sensitive to the ratio or amount of the two Twist dimers. FGFR1, whose expression does not overlap with Twist in the sutures (Johnson et al., *Mech Dev* 91:341-5, 2000; Rice et al., *Development* 127:1845-1855, 2000), was expressed equivalently in all of the cell lines. The addition of BMP7 induced FGFR2 expression in control 10T1/2 cells, however TE expression inhibited this induction. Therefore, T/T and T/E dimers have opposing effects on FGFR2 expression.

Example 6

T/T and T/E Regulated Genes are Altered in Twist +/− Mice

Figure 3D:
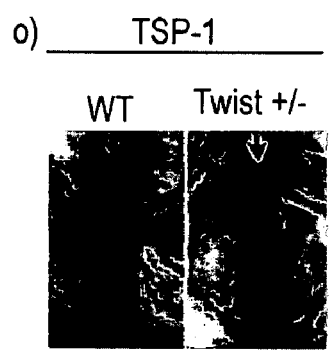
Figure 6A:
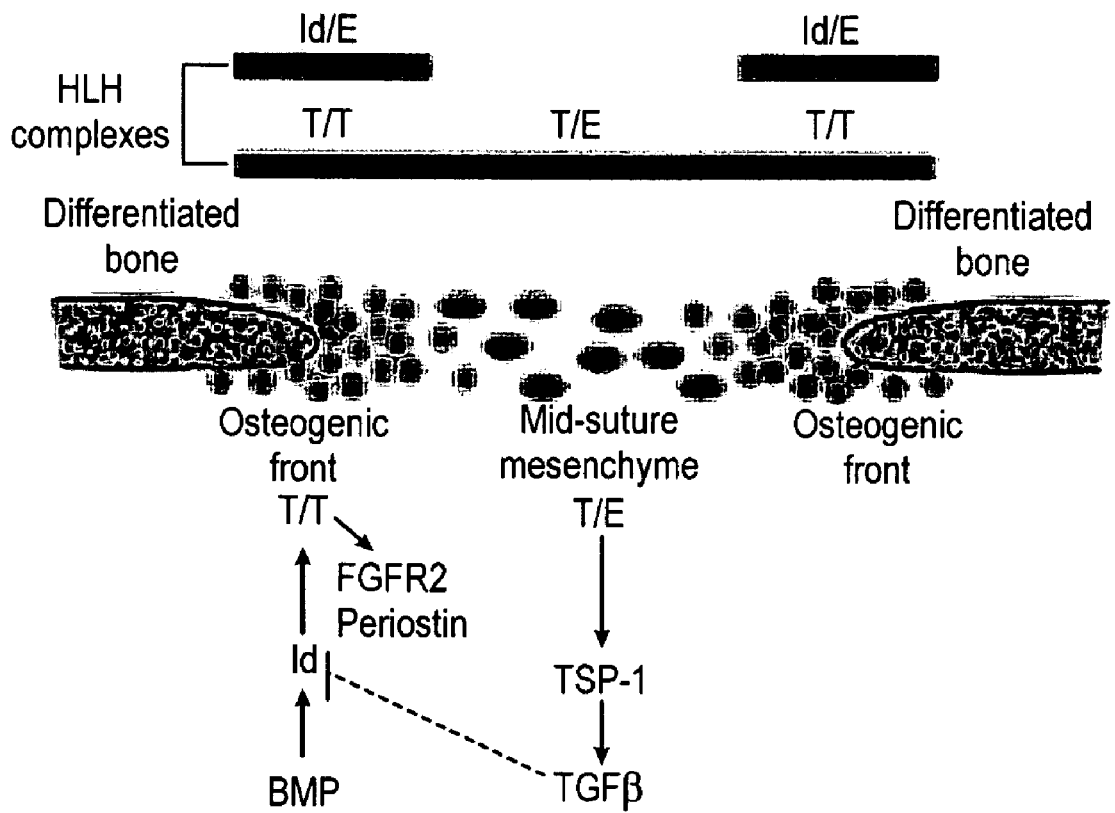
FIG. 6 shows a model of the regulation of cranial suture patency by Twist. (a) T/E heterodimers induce TSP-1 expression in the mid-suture mesenchyme, which then activates latent TGFβ and inhibits differentiation. BMP and TGFβ activity may coordinately restrict Id expression to the osteogenic fronts. Id expression promotes T/T homodimer formation, which enhances FGFR2 expression, further driving the formation of the osteogenic fronts. Changes in FGF, BMP or TGFβ levels would then alter the balance between T/E and T/T to either enhance or inhibit suture closure. (b) Proposed mechanism promoting craniosynostosis due to Twist haploinsufficiency. Graph of the relative levels of Id and Twist across the suture shown in (a). In the osteogenic fronts where Id levels are higher than Twist T/T dimers form while T/E dimers form in the mid-suture. When Twist levels are lowered due to haploinsufficiency the area where Id is higher than Twist expands towards the mid-suture.
Figure 6B:
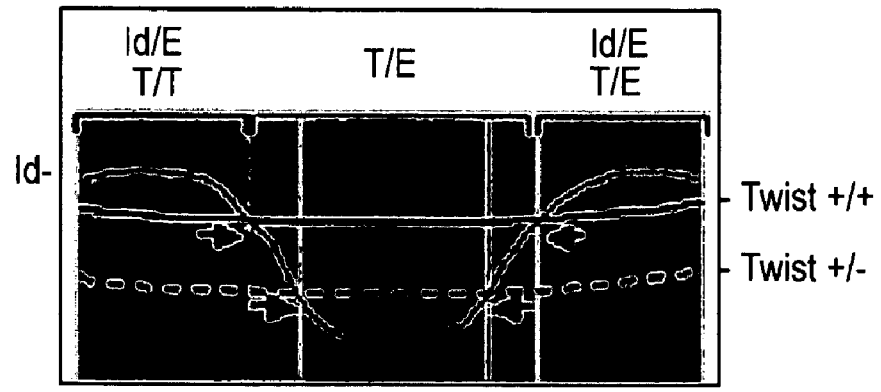
Figure 7A:
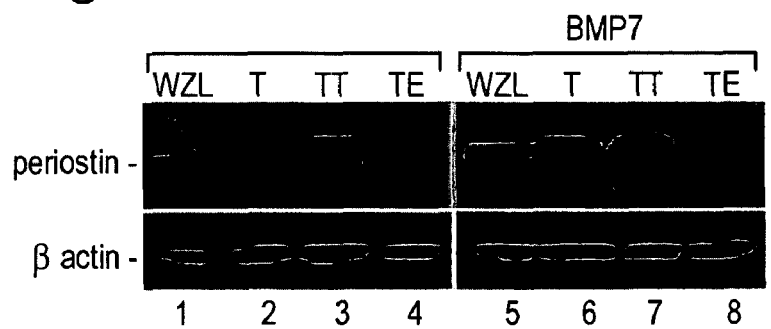
FIG. 7 shows Twist dimers differentially regulate gene expression (a) TT enhanced periostin expression while TE cells inhibited it. C3H10T1/2 cells were infected with a control retrovirus (WZL) or with one expressing TWIST (Tw), TT (TT), or TE (TE) and were grown in 10% FBS without or with 100 ng/ml BMP7 for 4 days and then assayed for periostin and □actin expression by western blot analysis. (c) Id1 is upregulated by BMP signaling. 10T1/2 cells were grown in 10% FBS without or with 100 ng/ml BMP7 for 4 days and then assayed for Id1, Id3, and GAPDH expression by RT-PCR. (d) TE induced Thrombospondin 1 (TSP-1) expression. 10T1/2 cell lines were grown in 10% FBS for 48 hours and then assayed for TSP-1 expression by immunofluorescence. (e) 10T1/2 cell lines were grown in 0.2% FBS for 48 hours and then the conditioned media was assayed for TSP-1 expression by western blot analysis following concentration on a heparin-sepharose column and elution with 1.5 M NaCl.
Figure 7B:
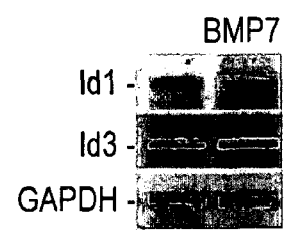
Figure 7C:
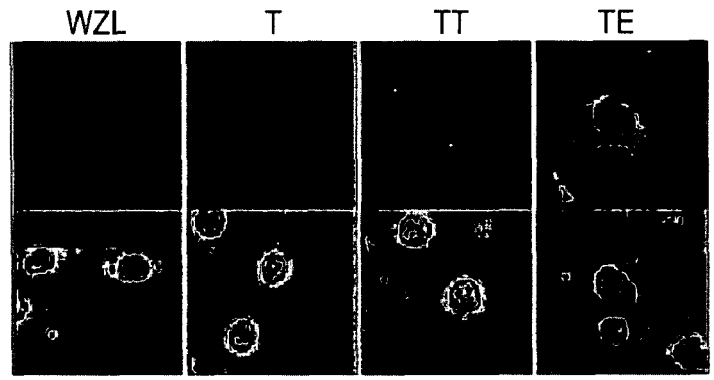
Figure 7D:
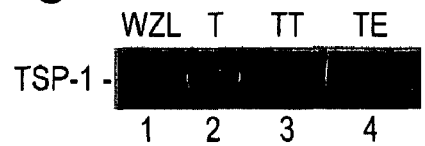
Figure 8:
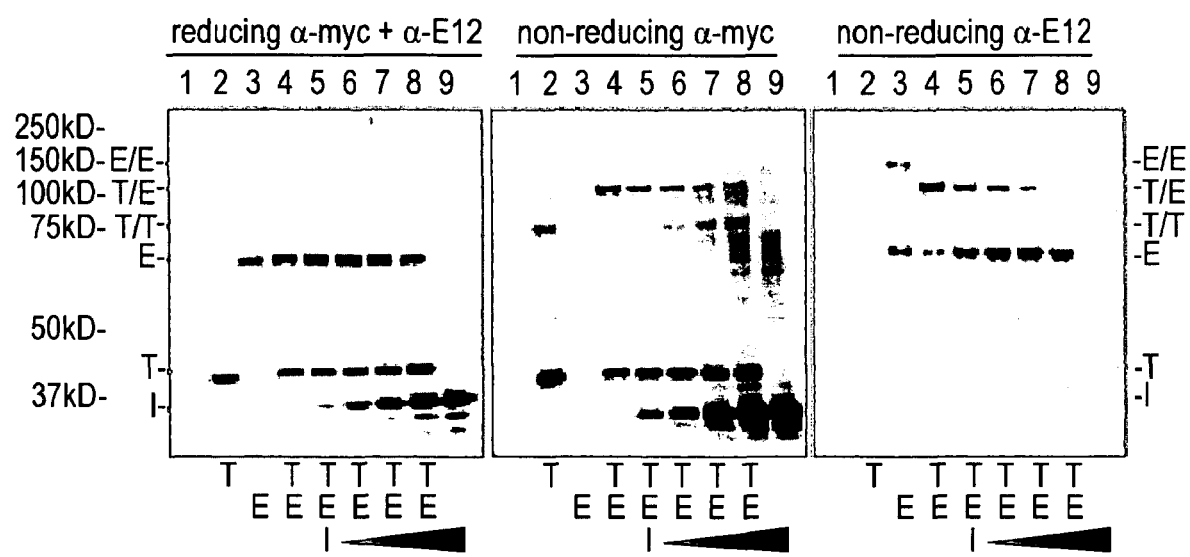
FIG. 8 shows Id levels alter the ratio of T/T and T/E dimers. 293 cells were transfected with Twist (T), E12 (E), and Id1 (I)-expressing plasmids as indicated. Id1 levels were 0.25, 0.5, 1, and 2-fold the level of Twist and E12 in lanes 5-8, respectively. For the two right gels samples were prepared without β-mercaptoethanol and were not heated prior to loading but were the same as the reducing gel on the left in all other respects. The Twist and the Id1 proteins contained myc-epitope tags and were detected with 9E10 anti-myc monoclonal antibodies in the left and right blots. E12 proteins were detected with anti-E2a polyclonal antibody in the center and right blots. The sizes for the T, E, and I monomers and the T/T, T/E and E/E dimers are indicated on the sides.

The mechanism that promotes craniosynostosis due to TWIST haploinsufficiency is still unclear but we suggest that the decrease in the level of Twist alters the balance between T/T and T/E dimers in the sutures resulting in a change of gene expression and cell behavior. The expansion of FGFR2 expression into the mid-suture (Rice et al., *Development* 127: 1845-1855, 2000), suggests that there is an increase in T/T formation in the sutures of Twist +/− mice. We propose that this is due to Id levels being relatively higher than Twist in a larger area resulting in less free E proteins being available for dimerization with Twist (see, FIG. 6b). To test this hypothesis we examined the expression of T/T and T/E-regulated genes in the sutures of wild type and Twist +/− mice. We confirmed the expansion of FGFR2 expression in the sagittal suture of Twist +/− mice and found that the expression of periostin also expanded towards the mid-suture, consistent with an increase in T/T formation (FIG. 3a). While there seemed to be a decrease in the level of periostin expression in the coronal suture the expression domain of both periostin and FGFR2 expanded to cover the entire suture. More dramatically, there was a significant decrease in TSP-1 expression in the sagittal suture of Twist +/− mice (FIGS. 3a and 3d), indicating a decrease in T/E dimers.

Figure 3E:
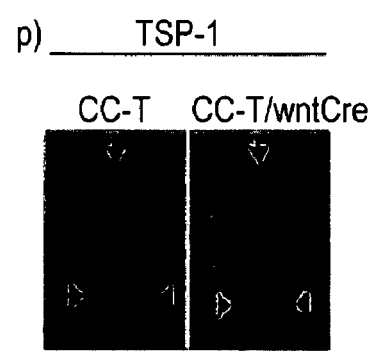

We next performed the converse experiment by increasing Twist expression in the cranial neural crest which gives rise to these sutural cells (Jiang et al., *Dev Biol* 241:106-16, 2002), a condition that we predict would increase T/E dimer formation. Indeed, we found that TSP-1 expression was induced in the osteogenic fronts of these mice (FIG. 3e). The full phenotype of these mice will be described elsewhere. Therefore, decreased and increased levels of Twist in the cranial sutures change the expression of the genes regulated by the T/T and T/E dimers in a predicted manner that supports our hypothesis.

Example 7

Twist Requires Heterodimerization to Inhibit Osteoblast Differentiation

Figure 4A:
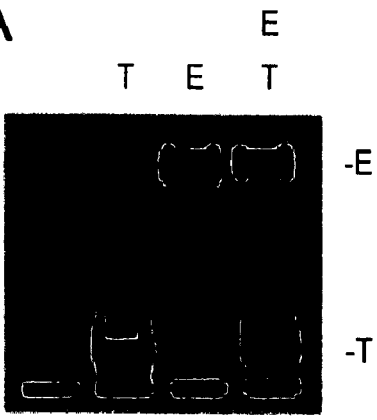
FIG. 4 shows E12 is required for Twist to inhibit osteoblast differentiation. Primary calvaria cells were infected with adenovirus expressing myc-Twist (T) and or myc-E12 (E) as indicated above gels. GFP-expressing adenovirus was used as a control where no virus is indicated. Cells were placed in differentiation medium for the indicated times before being harvested for (a) western analysis for myc-Twist (T) and myc-E12 (E) or (b) RT-PCR analysis for Runx2, α1(I) collagen (Col 1a1), bone sialoprotein (BSP), osteocalcin (OC), endogenous Twist, and GAPDH transcripts.
Figure 4B:
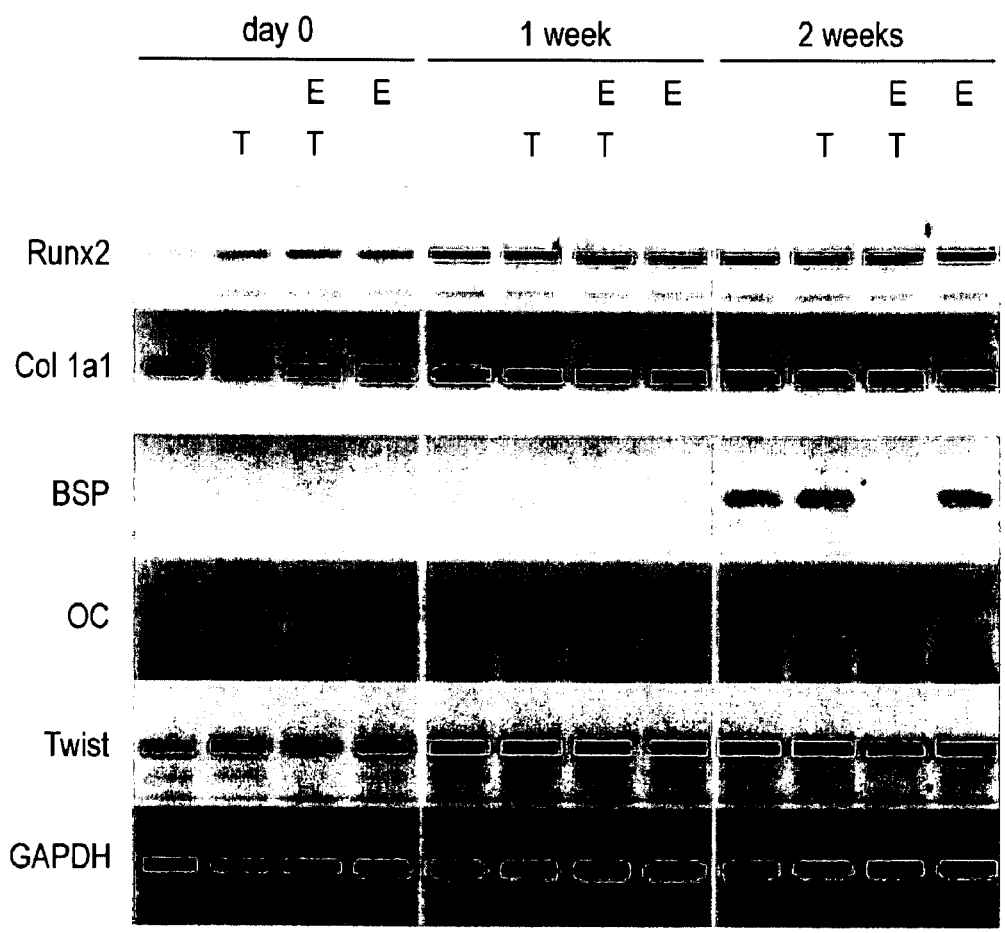

We next asked whether the Twist dimers differentially affected osteoblast differentiation. Overexpression of Twist has been shown to negatively regulate osteoblast differentiation (Funato et al., *Mol Cell Biol* 21:7416-28, 2001; Lee et al., *J Cell Biochem* 75:566-77, 1999) and osteoblasts isolated from individuals that were haploinsufficient for TWIST differentiated faster than control cells (Yousfi et al., *J Clin Invest* 107:1153-1161, 2001). Furthermore, Twist has recently been implicated in directly inhibiting the activity of the transcription factor Runx2, which promotes osteoblast differentiation (Bialek et al., *Dev Cell* 6:423-35, 2004). Runx2-dependent osteoblast differentiation, however, initiates in the osteogenic fronts where Twist is expressed. We therefore determined whether Twist required heterodimerization to inhibit osteoblast differentiation. In order to address this, primary calvaria cells were infected with adenovirus expressing Twist or E12 alone or in combination. Equal levels of myc-tagged Twist and E12 were expressed following 2 weeks of differentiation (FIG. 4a). Surprisingly, we found that cells transduced with a Twist-expressing adenovirus alone were not inhibited from differentiating as Runx2, □1(I) collagen, bone sialoprotein (BSP) and osteocalcin (OC) transcripts were all induced (FIG. 4b). The combination of Twist and E12, however, inhibited the later markers of osteoblast differentiation (BSP and OC), but did not affect the expression of the early markers (Runx2 and α1(I) collagen). E12 alone inhibited the expression of OC and this may have been due to it dimerizing with the endogenous Twist proteins that were expressed at high levels at that time (FIG. 4b). These results indicate that, similar to its inhibition of myogenesis (Spicer et al., *Science* 272:1476-1480, 1996), the inhibitory effect of Twist on osteogenic differentiation is mediated by the T/E dimer.

Example 8

Promotion of T/E Formation Prevents Suture Fusion in Twist +/− Mice

Figure 5:
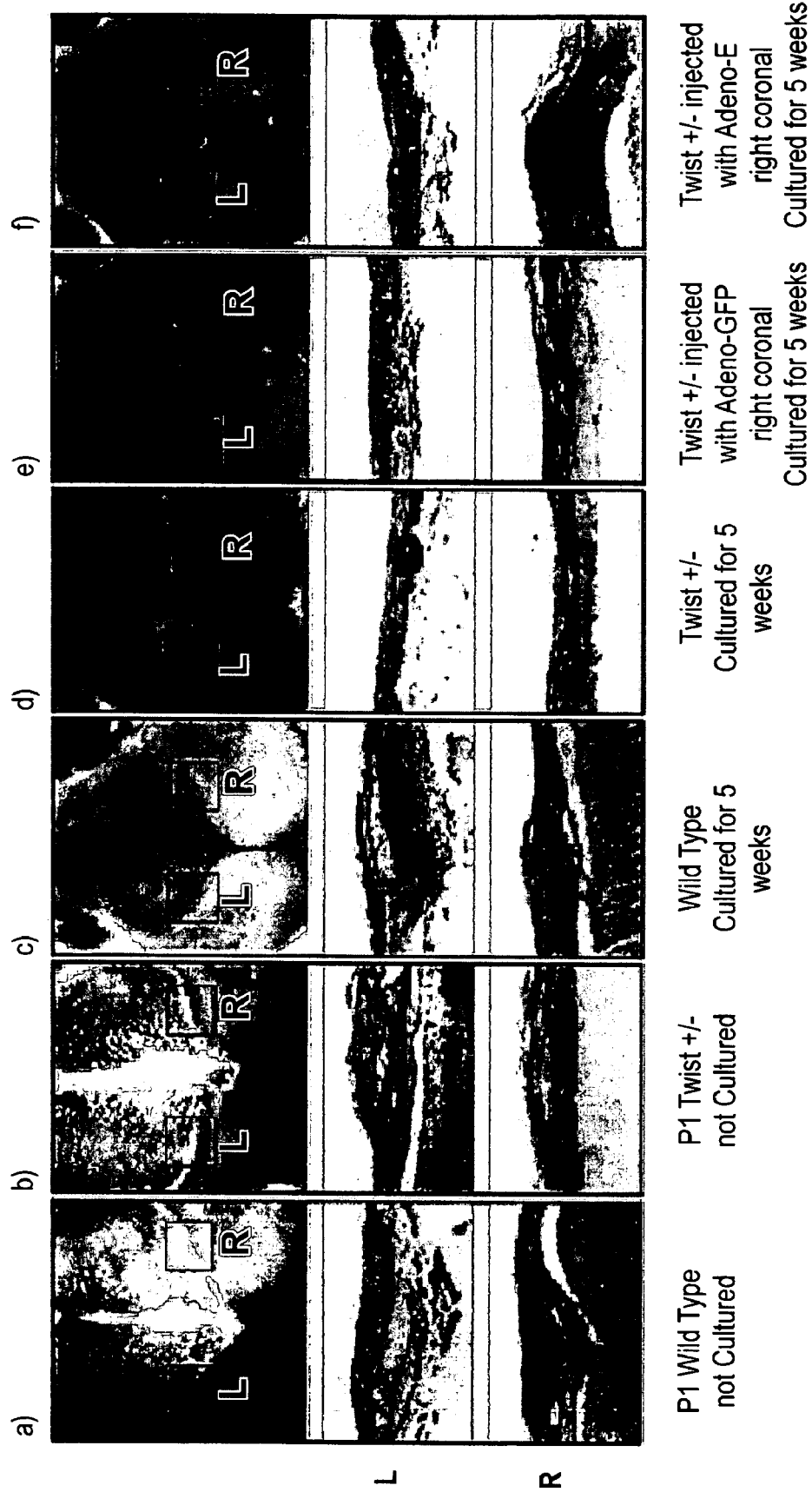
FIG. 5 shows promotion of T/E dimer formation prevents suture fusion in Twist +/– mice. Skulls of wild type (a) and Twist +/– (b) P1 mice. (c-f) Skull explants from P1 wild type (c) and Twist +/– (d-f) mice grown in culture for 5 weeks. Skulls were processed with alizarin red and then paraffin sectioned. Sections were then treated with von Kossa stain to indicate calcified bone (black staining). Sections through the left (L) and right (R) coronal sutures are shown below skulls. The right coronal suture of (e) and (f) was injected with adenovirus expressing either GFP (e) or E12 (f) at the time of explant. Note the fusion of the sutures in the Twist +/– skulls and the lack of fusion in the right coronal suture injected with Ad-E12 (f).

Our data suggests that there is an increase in the ratio of T/T to T/E in the sutures of Twist +/− mice that drives craniosynostosis. We therefore asked whether we could prevent suture fusion in these mice by altering E protein or Id levels to promote the formation of T/E dimers. To increase E protein expression we infected the sutures of Twist +/− mice with an adenovirus expressing E12. As in humans, Twist haploinsufficiency promotes the fusion of primarily the coronal suture, and therefore we focused our analysis on this suture. Since the coronal suture of live pups is hard to discern we utilized explant culture of the skull (Ogle, *Methods Mol Biol* 136:55-59, 2000). The sutures of Twist +/− mice do not fuse until 3-4 weeks after birth (Carver et al., *Anat Rec* 268:90-2, 2002), so we altered the culture conditions to try and maintain skull morphology during 4-5 weeks in culture. This was achieved by sectioning the skull horizontally from the base of the nose to the occipital bone, leaving the dura mater and brain intact (FIG. 5). Following 5 weeks in culture the skulls of wild type mice looked remarkably normal, with both the sagittal and coronal sutures remaining patent (FIG. 5c). The coronal sutures of Twist +/− mice are patent and relatively normal at birth (FIG. 5b), however after 5 weeks in culture distinct fusion of this suture was observed in 10 of 13 explants. In 3 of 4 uninjected Twist +/− control explants and 3 of 4 Twist +/− explants injected in the right coronal suture with adenovirus expressing GFP both the left and right coronal sutures had fused and the sagittal suture remained patent (FIGS. 5d and 5e). When the right coronal suture was injected with adenovirus expressing E12 at the time of explant, however, this suture failed to fuse in 4 of 5 Twist +/− skulls (FIG. 5f).

As another means to promote T/E formation we lowered Id levels by crossing Twist +/− mice with Id-null animals. Id3 has a similar expression pattern as Id1 in the cranial sutures (the antibody in FIG. 3 recognizes all Id proteins and data not shown) and since Id1 −/−;Id3 +/− mice are viable (Lyden et al., Nature 401:670-677, 1999), we decided to remove from 1 to 3 alleles of Id1 and Id3 genes on the Twist +/− background. As can be seen in Table 1, there was a significant decrease in the percentage of mice showing any coronal suture fusion as the number of Id alleles was removed. Approximately 87% of Twist +/− mice had craniosynostosis 5 weeks after birth and this decreased to 0% when three Id alleles were removed. To achieve a more accurate assessment of the degree to which craniosynostosis was rescued on the different genetic backgrounds we used a craniosynostosis index (CI) similar to one used to analyze Twist and Snail genetic interactions (Oram and Gridley, Genetics 170:971-974, 2005). Left and right coronal sutures were assessed individually and assigned a number between 0 (completely unfused) to 3 (completely fused) and the CI given in Table 1 indicates the average degree of craniosynostosis for a coronal suture on the indicated genetic background. As can be seen from the large standard deviation of the CI for Twist +/− mice, the degree of suture fusion was quite variable. This was also true with Twist +/−; Id1 +/− mice, however there was a noticeable decrease in the severity of suture fusion but the difference was not significant. The removal of two Id alleles, either Twist +/−;Id1 −/− or Twist +/−;Id1 +/−;Id3 +/−, however, produced almost a full rescue decreasing the CI from 1.64 for Twist +/− to 0.07. We have only obtained 5 Twist +/−;Id1 −/−;Id3 +/− mice so far but all of these have completely patent and normal looking sutures. Therefore, conditions that promote T/E formation, either increasing E proteins or decreasing Id levels, result in the inhibition of suture fusion in Twist +/− mice.

Example 9

The Role of Twist in Metastasis

Figure 11:
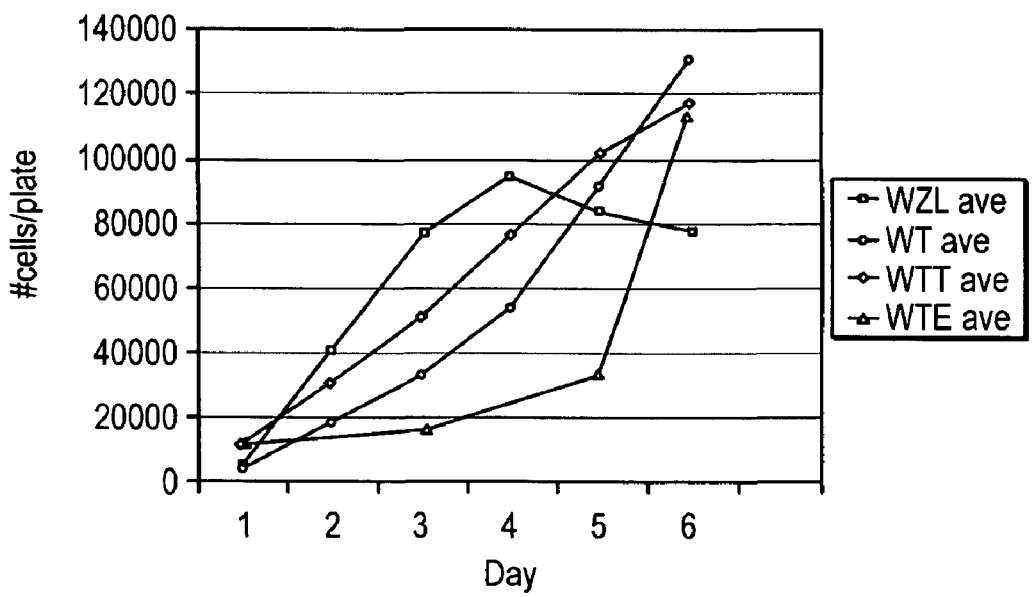
FIG. 11 shows subconfluent PyVT tumor cells infected with the same viruses as in FIG. 1 were plated in 10% FBS and cells from triplicate plates were counted daily for 6 days. Cells became confluent by day 5. TE expression inhibited proliferation before confluence but had little effect after confluence.
Figure 10:
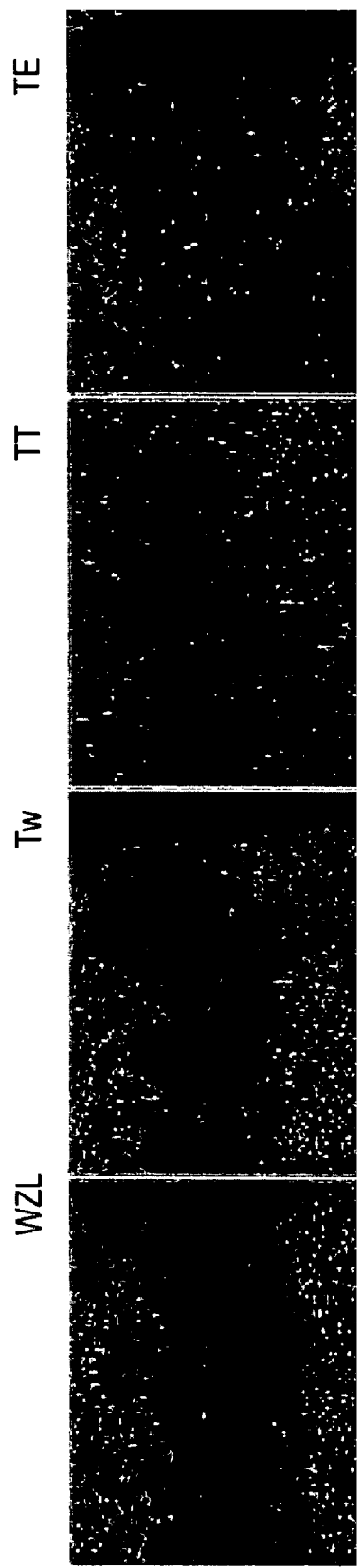
FIG. 10 shows PyVT tumor cells infected with the same viruses as in FIG. 1 were grown to confluence. A scratch was made across the plates and cell migration into the cleared area was monitored. Pictures were taken 48 hours post-scratch. Note promotion of migration by TT and inhibition by TE.
Figure 12:
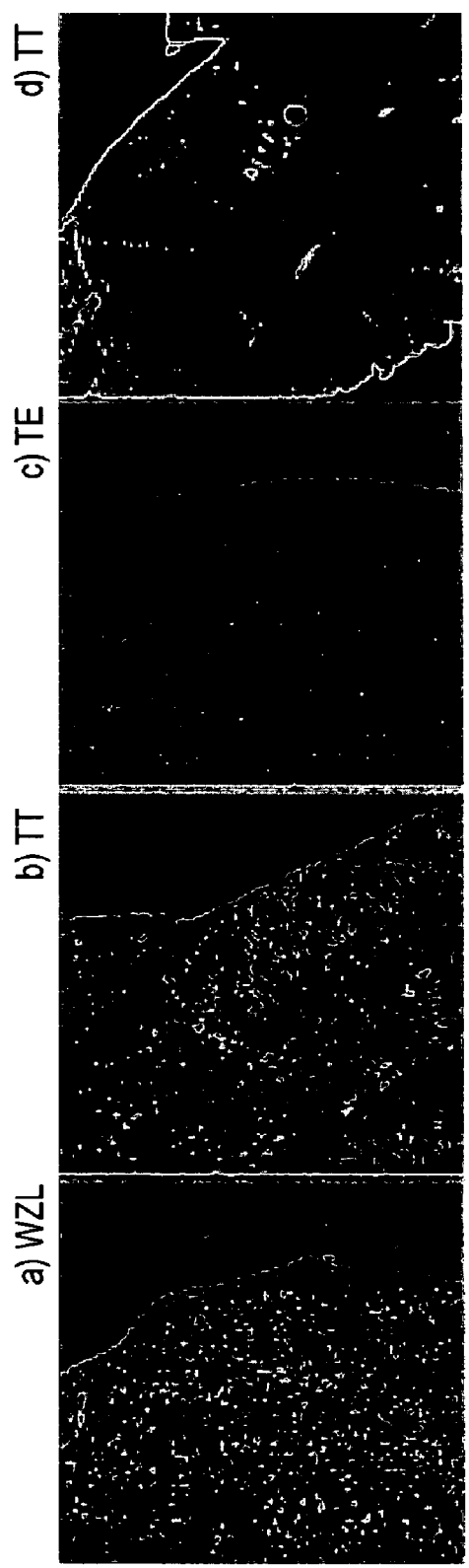
FIG. 12 shows the PyVT tumor cells in FIG. 2 were injected subcutaneously into nude mice (5 mice/line) and tumors were allowed to grow for 2 weeks. Tumors were sectioned in paraffin and stained for PECAM as a measure of vascularity (a-c) or with a trichrome stain. Note the compactness and the comparative lack of PECAM staining (brown stain) of the TE tumor (c), and invasiveness of the TT tumor into muscle tissue, which was not seen in any of the tumors derived from the other cell lines (d).

Metastasis involves several steps including invasion of the tumor into surrounding tissues, intravasation from the tumor into the vasculature, survival in the vasculature, extravasation into target tissues, and growth at the ectopic site. Twist has been implicated as promoting the early invasion and intravasation steps of metastasis (Yang, et al., Cell, 2004, 117:927-939, 2004). To determine if the Twist dimers differentially affect these stages of tumor progression we expressed the different Twist dimers in a breast tumor cell line derived from the MMTV-PyVT mice and have begun to characterize these lines. As we have found with other cell types, the expression of TT promoted cell migration while TE inhibited both migration and proliferation (FIGS. 10 and 11). Furthermore, subcutaneous tumors derived from TT-expressing cells were highly vascular and had invaded into muscular tissue, which we did not observe with any of the other tumor lines. Interestingly, tumors from TE-expressing cells were very encapsulated and had regions that lacked any vasculature suggesting that T/E dimers may even be inhibitory to tumor progression (FIG. 12). These phenotypes are suggestive of T/T promoting a more metastatic phenotype and T/E inhibiting this phenotype.

Breast cancer is among the most common human cancers, affecting up to 1 in every 8 women. Tumor metastasis is the major cause of death from breast cancers and while there have been improvements in diagnosis and treatment it is still unclear which molecular changes in breast tumors are likely to lead to invasion and metastasis. Therefore, there is still a need for a more detailed understanding of the mechanisms of metastasis in order to identify better diagnostic markers and therapeutic approaches. The transcription factor Twist is over-expressed in many cancers, including breast cancers, and its expression has generally been correlated with more aggressive tumor phenotypes. For instance one breast cancer study found increased Twist in 70% of invasive lobular carcinomas, 32% of invasive ductal carcinomas, and 30% of mixed ductal/lobular carcinomas, but it was not increased in non-metastatic tumors. Furthermore, decreasing Twist expression in one tumor line inhibited metastasis, implicating Twist as a mediator of this process, however the mechanisms underlying its actions are still unclear (Yang, et al., Cell, 927-939, 2004). We have been studying the transcriptional regulation of mesenchymal cell specification and differentiation, focusing on the role that Twist plays in these processes. Our recent findings, detailed below, provide a mechanistic understanding of Twist function, which can be utilized as a target to regulate metastatic cell behavior. We show here our model of Twist regulation as a means to control cancer (e.g., breast cancer) progression.

Figure 13:
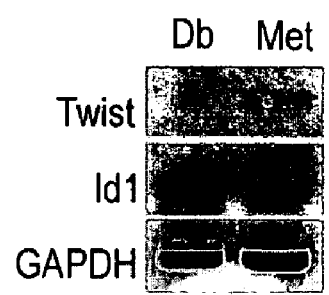
FIG. 13 shows Twist and Id1 are only expressed in the Met cell line. RNA was isolated from Db and Met cells and analyzed for Twist. Id1 and GAPDH by RT-PCR. Therefore, Twist and Id1 expression correlate with the metastatic phenotype of the cell lines.

To conduct the next Examples, we utilized the MMTV-PyVT mammary tumor model, which is one of the best murine models to mimic the human disease (Lin, et al., Am. J. Pathol. 163:211302126, 2003). These make use of two cell lines generated from mammary tumors from MMTV-PyVT transgenic mice either expressing the wild type PyVT (Met cells) or from mice expressing a mutant form of PyVT that can no longer activate P13 kinase (Db cells). Both lines form primary mammary tumors equally well, however the Db line is defective in the invasion and intravasation steps of metastasis (Jessen, et al., Cancer Res. 6:R157-169, 2004), and only form metastases to the lung 9% of the time whereas the wild type PyVT promotes metastasis 100% of the time (Webster, et al., Mol Cell Biol. 18:2344-2359, 1998). This defect is remarkably similar to a breast tumor line that normally metastasized very well but was inhibited in these early steps of metastasis by a siRNA directed to the Twist mRNA (Yang, et al., Cell, 927-939, 2004). Interestingly, we have found that Twist and Id1 are only expressed in the Met cells and not in the Db cell line (FIG. 13). Therefore, we feel that these lines represent an excellent model to characterize the role of Twist and Twist dimerization in metastasis.

Example 10

The Effect of Twist Dimers on Metastatic Cell Growth

In this Example we compare the effects of the expression of Twist, TT and TE on the cell behavior and metastatic ability of these two cell lines. Our preliminary data indicate that T/T dimers promote tumor cell migration and invasion while T/E dimers may inhibit both of these processes (FIGS. 10 and 12). These experiments were performed using a cell line derived from tumors from mice with the wild type MMTV-PyVT transgene indicating that the Twist dimers have a dominant activity in an already aggressive tumor cell. The experiments proposed here extend these observations to the effect of the Twist dimers on the Met and Db breast tumor lines. The use of these lines allows us to use T/T dimers to promote the early steps of metastasis in a non-metastatic tumor line (Db) and to use T/E dimers to prevent tumor progression in a highly metastatic tumor line (Met). Since Twist is only expressed in the Met cell line (FIG. 7) Twist expression is knocked down (i.e., knocked out) in these cells to determine the requirement of Twist for metastasis of these cells.

These experiments are initiated by infecting the Met and Db cell lines with pWZL retroviruses expressing Twist, TT, TE, or a short hairpin RNA (shRNA) directed against Twist (Yang, J., et al., Cell, 117:927-939, 2004). We modify these viruses so they contain an IRES-dsRed cassette allowing infected cells to be selected for red fluorescence by FACS (fluorescence activated cell sorter) cell sorting. The red fluorescence of the cells enhances our ability to detect metastatic nodules in the lung. After sorting, cells are monitored for Twist expression by immunofluorescence and western analysis. We then determine the effects of the expression of the various forms of Twist on cell proliferation, using cell counts (as in FIG. 11) and BrdU incorporation analysis and migration, using the scratch/wound assay (as in FIG. 10) and modified Boyden chamber assay. T/T dimers enhance migration and T/E dimers inhibit both migration and proliferation. Consistent with this, Met cells, which express Twist and Id1, have enhanced migration compared to Db cells (Jessen, K. A., et al., Breast Cancer Res, 6:R157-169, 2004). Interestingly, expression of TE inhibited the proliferation of the MMTV-PyVT cells before the cells reached confluence but after confluence the cell numbers ended up being close to the other lines (FIG. 11). This is consistent with the fact that tumors derived from these cells were the same size as those from all of the other lines. Therefore, growth after confluence in vitro can be used as an indicator of tumor growth in vivo.

Our previous experiments looking at the effects of Twist on tumor formation were done by subcutaneous injection of the tumor cells. While this method can give an indication of certain aspects of tumor growth and perhaps tumor invasion, subcutaneous tumors rarely metastasize and therefore are not a good model for our studies. Recently, one of our collaborators trained members of my lab in injection of tumor cells into the mammary fat pad. This method involves all the steps of metastasis and is the correct microenvironment for these tumors to form. Another advantage of using the tumor cells from the MMTV-PyVT mice is that these mice are on an FVB strain background. This enables us to use FVB mice as the recipients instead of having to use immuno-compromised mice such as nude or SCID mice. Immune response plays an important role in tumor progression and is lacking in these other mouse models. We follow the protocol used by the group that derived these lines and we will use 5 mice/cell line (Jessen, K. A, et al., Breast Cancer Res, 6:R157-169, 2004). Cells are resuspended in matrigel and $2 \times 10^6$ cells are injected into the #4 mammary fat pad. Primary tumors will be removed when they reach 1.5 cm (about 3 weeks). The mice are then harvested at 42 days post-injection and the lungs are analyzed to identify and enumerate metastases. Primary tumor and metastatic growth is analyzed for proliferation, apoptosis, vasculature, differentiation and markers of tumor structure such as laminin and E cadherin. RNA is also be isolated to analyze gene expression.

Example 11

Analysis of Twist Mediated Gene Expression

In this example we perform gene expression analysis to identify genes that are differentially regulated by the Twist dimers and that correlate with metastatic potential. A critical need in diagnosing the metastatic potential of breast tumors is the identification of molecular markers that will accurately predict this potential. Our preliminary data indicates that T/T dimers promote invasiveness and potentially metastasis while T/E dimers prevent these (FIGS. 10 and 12) and therefore the genes that are differentially regulated by these dimers may be good diagnostic indicators of the metastatic potential of a tumor. For this analysis we use the RNA isolated from the primary tumors from the Db and Met cell lines from Example 10 for microarray analysis instead of from the cell lines grown in vitro because the host tissue environment can drastically influence their metastatic abilities and their gene expression profiles.

However, to ensure that we are analyzing RNA from the tumor cells, and not host tissues, the tumors are dissociated and FACS sorted for the expression of the viral dsRED protein. Three tumors derived from each cell line (WT, TT, TE, and Twist shRNA for Db and Met lines) are analyzed for a total of 24 samples. We utilize the Norris-Cotton Cancer Center Microarray Core Facility at Dartmouth Medical Center to hybridize and analyze the samples using the Affymetrix mouse gene chip 430 2.0, which contains 45,000 probe sets to analyze the expression level of over 39,000 transcripts and variants from over 34,000 well characterized mouse genes. Data is analyzed using Gene Traffic, OntoExpress and PathwayAssist with the help of Core Facility personnel. We are particularly interested in genes that are found in TT-expressing Db cells and wild type Met cells but are not in wild type Db cells or Twist shRNA-expressing cells. This gene profile represents a good diagnostic indicator of metastatic potential. Expression of genes in this category will be verified by RT-PCR and perhaps quantitative PCR. Tumors that were not analyzed by microarray are analyzed for this gene set and the expression of these genes is correlated with the metastatic character of the tumors to determine which genes correlate with metastatic phenotype.

Example 12

The Effect of Twist Dimer Expression on De Novo Tumor Growth

Example we characterize the effects of Twist dimer expression on de novo tumor growth and metastasis in MMTV-PyVT mice. In Examples 10 and 11 we characterized the effects of different forms of Twist on gene expression and on the behavior of cells that are already tumorigenic and therefore the findings may be dependent on the cell line used. This Example is designed to address this criticism by looking at the effects of the Twist dimers on in situ tumor growth and progression in the MMTV-PyVT mice. In this Example we express Twist, TT or TE specifically in the mammary gland of MMTV-PyVT mice to see if their expression alters the progression through all four stages of tumorigenesis in these mice. We have generated mice containing Cre recombinase-inducible transgenes (CAGCAT [SEQ ID NO.: 14]) that express Twist, TT or TE following recombination, and these all give significant phenotypes when crossed with mice expressing Cre in neural crest cells. We have crossed the MMTV-PyVT mice with mice containing an MMTV-Cre transgene and are now crossing the MMTV-PyVT/MMTV-Cre mice with our CAGCAT [SEQ ID NO.:14]-Twist, TT and TE mice to specifically induce the Twist transgenes in the mammary epithelium. The female offspring are monitored by palpation for the initiation of mammary hyperplasia. Our Institute has recently installed a small animal MRI, which may also be used to monitor tumor progression. 5 mice/line are sacrificed at different time points from 4 weeks to 16 weeks.

Primary tumor and metastatic growth are analyzed as in Example 10 for proliferation, apoptosis, vasculature, differentiation and markers of tumor structure such as laminin and E cadherin. Primary tumors are also be analyzed for the expression of the gene set outlined in Example 11.

It is apparent form the forgoing that the present invention provides to those skilled in the art compositions and methods for the modulation of metastatic and mesenchymal cell growth and mobility via the regulation of the formation of Twist/Twist homodimers and Twist/E heterodimers. The present invention also provides to those skilled in the art methods for screening agents and agent libraries for molecules that function to modulate the formation of Twist/Twist homodimers, Twist/E protein heterodimers or their upstream or downstream effector molecules.

I claim:

1. A method of decreasing the mammalian Twist/mammalian Twist homodimer ratio relative to the mammalian Twist/E2A protein heterodimer ratio in a metastatic cell comprising contacting cells selected from a group consisting of metastatic cells in a mammal, cells in a mouse or in vitro cell lines with an agent characterized by the ability to decrease the ratio of mammalian Twist/mammalian Twist homodimers to mammalian Twist/E2A protein heterodimers in the cells, wherein said agent has been selected by a method comprising:
   a) providing the agent to be screened for the ability to decrease the ratio of mammalian Twist/mammalian Twist homodimers to mammalian Twist/E2A protein heterodimers;
   b) forming a reaction mixture comprising the agent to be screened for the ability to decrease the ratio of mammalian Twist/mammalian Twist homodimers to mammalian Twist/E2A protein heterodimers, and a mixture of mammalian Twist and E2A proteins;
   c) incubating the reaction mixture of step b) for a period of time and under conditions appropriate for the formation of mammalian Twist/mammalian Twist homodimers and mammalian Twist/E2A protein heterodimers;
   d) determining the ratio of homodimer to heterodimer following the incubation of step c);
   e) comparing the ratio of homodimer to heterodimer determined in step d) to the ratio detected in an otherwise identical incubation mixture which does not include an agent to be screened for the ability to decrease the ratio of mammalian Twist/mammalian Twist homodimers to mammalian Twist/E2A protein heterodimers, a substantial decrease in the ratio determined in step d) to that of the otherwise identical incubation mixture being indicative of the agent of step b) being characterized by the ability to decrease the ratio of mammalian Twist/mammalian Twist homodimers relative to mammalian Twist/E2A protein heterodimers and where in the agent is selected from one or more of a group consisting of gene expression constructs or inhibitory RNA molecules and said agent is characterized by the ability to promote mammalian Twist/E2A protein heterodimerization or by the ability to inhibit mammalian Twist/mammalian Twist homodimerization.

2. The method of claim 1 wherein the agent is a molecule characterized by the ability to inhibit mammalian Twist expression.

3. The method of claim 2 wherein the molecule is a siRNA.

4. The method of claim 1 wherein the agent is an expression construct encoding a functional E2A protein.

5. The method of claim 1, wherein said agent is an Id expression construct.

* * * * *